US012773324B2

(12) United States Patent
Woollen et al.

(10) Patent No.: US 12,773,324 B2
(45) Date of Patent: Oct. 27, 2026

(54) ORTHOPAEDIC SURGICAL CLAMP INSTRUMENTS FOR TAPER LOCKING THE COMPONENTS OF A HIP PROSTHESIS DURING A HIP REPLACEMENT SURGICAL PROCEDURE AND METHOD OF USING THE SAME

(71) Applicant: DePuy Ireland Unlimited Company, Ringaskiddy (IE)

(72) Inventors: Neil C. Woollen, Lincolnshire (GB); Caroline M. Wither, Christchurch (NZ)

(73) Assignee: DePuy Ireland Unlimited Company, Ringaskiddy (IE)

( * ) Notice: Subject to any disclaimer, the term of this patent is extended or adjusted under 35 U.S.C. 154(b) by 0 days.

(21) Appl. No.: 18/922,781

(22) Filed: Oct. 22, 2024

(65) Prior Publication Data

US 2026/0108363 A1 Apr. 23, 2026

(51) Int. Cl.
*A61F 2/46* (2006.01)
*A61F 2/30* (2006.01)

(52) U.S. Cl.
CPC .. *A61F 2/4607* (2013.01); *A61F 2002/30329* (2013.01)

(58) Field of Classification Search
CPC ................ A61F 2/46; A61F 2002/4622; A61F 2002/4625; A61F 2002/4627; A61F 2002/4628; A61B 17/8841; A61B 17/885
USPC ...... 606/86 A, 86 B, 99, 104, 105, 151, 157, 606/205, 207, 208, 324
See application file for complete search history.

(56) References Cited

U.S. PATENT DOCUMENTS

| | | | | |
|---|---|---|---|---|
| 5,284,487 | A * | 2/1994 | Hartmeister | B25B 7/12 606/205 |
| 5,308,357 | A * | 5/1994 | Lichtman | A61B 17/2909 606/208 |
| 5,899,901 | A * | 5/1999 | Middleton | A61B 17/7082 606/86 A |
| 6,330,845 | B1 | 12/2001 | Meulink | |
| 6,871,549 | B2 | 3/2005 | Serra et al. | |
| 7,105,029 | B2 | 9/2006 | Doubler et al. | |
| 8,419,743 | B2 | 4/2013 | Smith et al. | |
| 8,518,050 | B2 | 8/2013 | McCleary et al. | |
| 8,533,921 | B2 | 9/2013 | Leisinger et al. | |
| 8,685,036 | B2 | 4/2014 | Jones et al. | |

(Continued)

OTHER PUBLICATIONS

Reclaim Revision Hip System Surgical Technique; DePuy Synthes 2017; 38 pages.

*Primary Examiner* — Eduardo C Robert
*Assistant Examiner* — Christina Negrellirodriguez
(74) *Attorney, Agent, or Firm* — Barnes & Thornburg LLP

(57) ABSTRACT

An orthopaedic surgical instrument assembly operable to taper lock orthopaedic components to one another includes a taper assembly instrument having a handle with a draw rod extending therethrough so as to be slidable relative to the handle and a clamp instrument configured to selectively engage the taper assembly instrument so as to move the draw rod relative to the handle. A sacrificial tensile bar component of the taper assembly instrument is configured to break when a predetermined load has been applied to the orthopaedic components. A method of using an orthopaedic surgical instrument assembly to taper lock orthopaedic components to one another is also disclosed.

13 Claims, 15 Drawing Sheets

(56) References Cited

U.S. PATENT DOCUMENTS

| | | | | |
|---|---|---|---|---|
| 8,998,948 | B2 * | 4/2015 | Hyodo .................. | A61B 17/29 606/147 |
| 9,119,601 | B2 | 9/2015 | McCleary et al. | |
| 9,314,287 | B2 | 4/2016 | Smith et al. | |
| 9,381,097 | B2 | 7/2016 | Jones et al. | |
| 10,201,374 | B2 | 2/2019 | Wagner | |
| 11,497,625 | B2 | 11/2022 | Huber et al. | |
| 2007/0078464 | A1 | 4/2007 | Jones et al. | |
| 2009/0112218 | A1 | 4/2009 | McCleary et al. | |
| 2010/0280560 | A1 * | 11/2010 | Brumfield .......... | A61B 17/7088 606/86 A |
| 2018/0193168 | A1 | 7/2018 | Termanini et al. | |
| 2019/0142608 | A1 | 5/2019 | Termanini et al. | |
| 2024/0091017 | A1 | 3/2024 | Kartholl et al. | |

* cited by examiner

ORTHOPAEDIC SURGICAL CLAMP INSTRUMENTS FOR TAPER LOCKING THE COMPONENTS OF A HIP PROSTHESIS DURING A HIP REPLACEMENT SURGICAL PROCEDURE AND METHOD OF USING THE SAME

CROSS REFERENCE

Cross reference is made to U.S. Patent Application Ser. No. 18/922,734, entitled "ORTHOPAEDIC TAPER ASSEMBLY INSTRUMENT FOR TAPER LOCKING THE COMPONENTS OF A HIP PROSTHESIS DURING A HIP REPLACEMENT SURGICAL PROCEDURE AND METHOD OF USING THE SAME" which is assigned to the same assignee as the present application, is filed concurrently herewith, and is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a hip replacement procedure.

BACKGROUND

During the lifetime of a patient, it may be necessary to perform a joint replacement procedure on the patient as a result of, for example, disease or trauma. The joint replacement procedure may involve the use of a prosthesis which is implanted into one of the patient's bones. In the case of a hip replacement procedure, a femoral prosthesis is implanted into the patient's femur. Such a femoral prosthesis typically includes a spherically-shaped head which bears against the patient's acetabulum, along with an elongated intramedullary stem which is utilized to secure the femoral component to the patient's femur. To secure the prosthesis to the patient's femur, the intramedullary canal of the patient's femur is first surgically prepared (e.g. reamed and/or broached) such that the intramedullary stem of the femoral prosthesis may be subsequently implanted therein.

During performance of such a hip replacement procedure, it is generally necessary to provide the surgeon with a certain degree of flexibility in the selection of a prosthesis. In particular, the anatomy of the bone into which the prosthesis is to be implanted may vary somewhat from patient to patient. For example, a given patient's femur may be relatively long or relatively short thereby requiring use of a femoral prosthesis which includes a stem that is relatively long or short, respectively. Moreover, in certain cases, such as when use of a relatively long stem length is required, the stem must also be bowed in order to conform to the anatomy of the patient's femur.

As a result, modular prostheses have been designed. As its name implies, a modular prosthesis is constructed in modular form so the individual components of the prosthesis can be selected to fit the needs of a given patient's anatomy. For example, a typical modular prosthesis includes a proximal body component that can be assembled to any one of numerous distal stem components. Such a design allows the distal stem component to be selected and thereafter implanted in the patient's bone in a position which conforms to the patient's anatomy while also allowing for a degree of independent positioning of the proximal body component relative to the patient's acetabulum.

SUMMARY

According to one aspect, an orthopaedic surgical clamp instrument operable to taper lock orthopaedic components to one another includes a first lever having a proximal end that includes an upper handle, and a distal end that includes a pivot flange link. A second lever is pivotally coupled to the first lever and includes a proximal end that includes a lower handle, and a distal end that includes a pivot flange link. An upper end of the pivot flange link of the second lever is pivotally coupled to a lower end of the pivot flange of the first lever. The clamp instrument also includes a first clamping jaw having a socket formed in a distal end thereof. The socket is configured to receive an orthopaedic taper assembly instrument therein. An upper end of the first clamping jaw is pivotally coupled to an upper end of the pivot flange link of the first lever. The first clamping jaw also includes a proximal end opposite its distal end. The clamp instrument also includes a second clamping jaw having a socket formed in a distal end thereof. The socket is configured to receive the orthopaedic taper assembly instrument therein. The second clamping jaw also includes a lower end pivotally coupled to a lower end of the pivot flange link of the second lever, and a proximal end opposite its distal end that is pivotally coupled to the proximal end of the first clamping jaw.

In an embodiment, movement of the upper handle and the lower handle toward one another causes movement of the socket of the first clamping jaw and the socket of the second clamping jaw away from one another.

The upper end of the pivot flange link of the second lever may be pivotally coupled to the lower end of the pivot flange of the first lever at a first pivot joint, with the proximal end of the second clamping jaw being pivotally coupled to the proximal end of the first clamping jaw at a second pivot joint. In such an embodiment, movement of the upper handle and the lower handle toward one another causes movement of the first pivot joint distally away from the second pivot joint.

Further, the upper end of the first clamping jaw may be pivotally coupled to the upper end of the pivot flange link of the first lever at a third pivot joint, with the lower end of the second clamping jaw being pivotally coupled to the lower end of the pivot flange link of the second lever at a fourth pivot joint. In such an embodiment, movement of the first pivot joint distally away from the second pivot joint causes movement of the third pivot joint away from the fourth pivot joint.

In an embodiment, the upper end of the first clamping jaw is pivotally coupled to the upper end of the pivot flange link of the first lever at a first pivot joint, with the lower end of the second clamping jaw being pivotally coupled to the lower end of the pivot flange link of the second lever at a second pivot joint. Movement of the upper handle and the lower handle toward one another causes movement of the first pivot joint away from the second pivot joint.

In an embodiment, the pivot flange of the first lever, the pivot flange of the second lever, the first clamping jaw, and the second clamping jaw define a four-bar linkage.

According to another aspect, an orthopaedic surgical instrument assembly operable to taper lock orthopaedic components to one another includes a taper assembly instrument having a handle with a draw rod extending therethrough so as to be slidable relative to the handle. The draw bar has a knob on its proximal end and a set of locking threads on its distal end. The surgical instrument assembly also includes a clamp instrument configured to selectively engage the taper assembly instrument so as to move the draw rod relative to the handle. The clamp instrument includes a first lever having a proximal end that includes an upper handle, and a distal end that includes a pivot flange link. The clamp instrument also includes a second lever pivotally coupled to the first lever. The second lever has a proximal end that includes a lower handle, and a distal end that includes a pivot flange link. An upper end of the pivot flange link of the second lever is pivotally coupled to a lower end of the pivot flange of the first lever. The clamp instrument also includes a first clamping jaw having a socket formed in a distal end thereof that is configured to receive the draw rod of the taper assembly instrument therein. The first clamping jaw also includes an upper end pivotally coupled to an upper end of the pivot flange link of the first lever, and a proximal end opposite its distal end. The clamp instrument also includes a second clamping jaw having a socket formed in a distal end thereof that is configured to receive the draw rod of the taper assembly instrument therein. The second clamping jaw also includes a lower end pivotally coupled to a lower end of the pivot flange link of the second lever, and a proximal end opposite its distal end that is pivotally coupled to the proximal end of the first clamping jaw.

In an embodiment, movement of the upper handle and the lower handle of the clamp instrument toward one another causes movement of the socket of the first clamping jaw and the socket of the second clamping jaw away from one another such that, when the draw rod of the of the taper assembly instrument is positioned in the socket of the first clamping jaw and the socket of the second clamping jaw, the knob of the taper assembly instrument is urged away from the handle of the of the taper assembly instrument.

In an embodiment, the upper end of the pivot flange link of the second lever is pivotally coupled to the lower end of the pivot flange of the first lever at a first pivot joint, with the proximal end of the second clamping jaw being pivotally coupled to the proximal end of the first clamping jaw at a second pivot joint. Movement of the upper handle and the lower handle toward one another causes movement of the first pivot joint distally away from the second pivot joint.

In an embodiment, the upper end of the first clamping jaw is pivotally coupled to the upper end of the pivot flange link of the first lever at a third pivot joint, with the lower end of the second clamping jaw being pivotally coupled to the lower end of the pivot flange link of the second lever at a fourth pivot joint. Movement of the first pivot joint distally away from the second pivot joint causes movement of the third pivot joint away from the fourth pivot joint.

In another embodiment, the upper end of the first clamping jaw is pivotally coupled to the upper end of the pivot flange link of the first lever at a first pivot joint, with the lower end of the second clamping jaw being pivotally coupled to the lower end of the pivot flange link of the second lever at a second pivot joint. Movement of the upper handle and the lower handle toward one another causes movement of the first pivot joint away from the second pivot joint.

In an embodiment, the pivot flange of the first lever, the pivot flange of the second lever, the first clamping jaw, and the second clamping jaw define a four-bar linkage.

According to another aspect, an orthopaedic surgical clamp instrument operable to taper lock orthopaedic components to one another includes a first clamping jaw having a socket formed in a distal end thereof that is configured to receive an orthopaedic taper assembly instrument therein, and a proximal end opposite its distal end. The clamp instrument also includes a second clamping jaw having a socket formed in a distal end thereof that is configured to receive the orthopaedic taper assembly instrument therein, and a proximal end opposite its distal end that is pivotally coupled to the proximal end of the first clamping jaw. The clamp instrument also includes a drive link operatively coupled to the first clamping jaw and the second connecting jaw. The drive link has a threaded bore formed therein. The clamp instrument also includes a drive screw having a connector configured to be secured to a rotary tool defined in its proximal end and a threaded shaft extending distally away from the connector. The threaded shaft of the drive screw is positioned in the threaded bore of the drive link. Rotation of the drive screw in a first direction causes the drive link to be moved in the direction away the sockets of the first and second clamping jaws thereby moving the first and second clamping jaws away from one another. Rotation of the drive screw in a second, opposite direction causes the drive link to be moved in the direction toward the sockets of the first and second clamping jaws thereby moving the first and second clamping jaws toward one another.

In an embodiment, the clamp instrument also includes a first connecting link and a second connecting link. An upper end of the first connecting link is pivotally coupled to the first clamping jaw, with a lower end of the first connecting link being pivotally coupled to the drive link. A lower end of the second connecting link is pivotally coupled to the second clamping jaw, and an upper end of the second connecting link is pivotally coupled to the drive link.

The upper end of the first connecting link may be pivotally coupled to the first clamping jaw at a first pivot joint, with the lower end of the second connecting link being pivotally coupled to the second clamping jaw at a second pivot joint. In such an arrangement, rotation of the drive screw in the first direction causes the first and second pivot joints to be moved away from one another thereby moving the first and second clamping jaws away from one another, whereas rotation of the drive screw in the second, opposite direction causes the first and second pivot joints to be moved toward one another thereby moving the first and second clamping jaws toward one another.

The lower end of the first connecting link and the upper end of the second connecting link may be pivotally coupled to the drive link at a third pivot joint, with the proximal end of the second clamping jaw being pivotally coupled to the proximal end of the first clamping jaw at a fourth pivot joint. In such an arrangement, rotation of the drive screw in the first direction causes the third and fourth pivot joints to be moved toward one another thereby moving the first and second clamping jaws away from one another, whereas rotation of the drive screw in the second, opposite direction causes the third and fourth pivot joints to be moved away from one another thereby moving the first and second clamping jaws toward one another.

According to another aspect, a taper assembly instrument operable to taper lock orthopaedic components to one another includes a proximal draw rod component that includes an elongated shaft having a set of threads formed in its proximal end, and a tensile bar slot formed in its distal end. The taper assembly instrument also includes a distal draw rod component that includes an elongated shaft having a set of threads formed in its distal end, and a tensile bar slot formed in its proximal end. The proximal end of the elongated shaft of the distal draw rod component abuts the distal end of the elongated shaft of the proximal draw rod component such that the elongated shafts of the proximal and distal draw rod components lie on a common longitudinal axis, and the tensile bar slots of the proximal and distal draw rod components open into one another. The taper assembly instrument also includes a sacrificial tensile bar component having a proximal end that is positioned in the tensile bar slot of the proximal draw rod component and a distal end positioned in the tensile bar slot of the distal draw rod component so as to couple the proximal and distal draw rod components to one another. The taper assembly instrument further includes a removable handle having a bore formed therethrough that extends from a proximal end of the handle to a distal end of the handle. The elongated shaft of the proximal draw rod component is received into the bore of the handle such that the threads formed in the proximal end thereof extend out of the proximal end of the handle. The handle has an elongated outer surface that extends parallel to the handle's bore and is configured to be gripped during use of the taper assembly instrument. The taper assembly instrument also includes a knob threadingly engaged to the set of threads formed in the proximal end of the proximal draw rod component such that movement of the knob relative to the handle causes movement of the set of threads formed in the distal end of the distal draw component relative to the handle.

In an embodiment, the bore of the handle has a longitudinal axis that is collinear with the common longitudinal axis upon which the elongated shafts of the proximal and distal draw rod components lie.

The taper assembly instrument may also include a tip component having an elongated hollow body defining an elongated bore, and a set of threads formed in an outer surface of a proximal end of the elongated body. The elongated shaft of the distal draw rod component may be received into the bore of the tip component such that the threads formed in the distal end thereof extend out of a distal end of the tip component. The set of threads formed in the outer surface of the proximal end of the tip component may be threadingly engaged to a set of threads formed in the distal end of the handle so as to removably secure the tip component to the handle.

In an embodiment, the bore of the tip component has a longitudinal axis that is collinear with the common longitudinal axis upon which the elongated shafts of the proximal and distal draw rod components lie.

The bore of the handle may also have a longitudinal axis that is collinear with the common longitudinal axis upon which the elongated shafts of the proximal and distal draw rod components lie.

In an embodiment, the distal end of the tip component has an annular collar formed therein that is configured to abut a superior end of an orthopaedic implant during use of the taper assembly instrument.

According to another aspect, a method of assembling a taper assembly instrument includes aligning a distal end of a proximal draw rod component with a proximal end of a distal draw rod component in a first position and pushing the two ends together. A proximal end of a sacrificial tensile bar component is inserted into a tensile bar slot formed in the proximal draw rod and a distal end of the tensile bar component into a tensile bar slot formed in the distal draw rod component. Thereafter, the proximal draw rod component is rotated relative to the distal draw rod component to a second position so as to couple the proximal and distal draw rod components to one another. A bore of a hollow handle is slid onto an elongated shaft of the proximal draw rod component such that a set of threads formed in a proximal end of the elongated shaft of the proximal draw bar component extends out of a proximal end of the handle, and a set of threads formed in a distal end of the elongated shaft of the distal draw bar component extends out of a distal end of the handle.

The method may also include securing a tip component to the handle such that the set of threads formed in the distal end of the elongated shaft of the distal draw bar component extends out of a distal end of the tip component. A knob may be secured to the set of threads formed in the proximal end of the elongated shaft of the proximal draw bar component.

The bore of the handle and the elongated shafts of the proximal and distal draw rod components may all lie on a common longitudinal axis when the handle is slid onto the proximal draw rod component.

An alignment indicator disposed on the distal draw rod component may be aligned with a first alignment indicator disposed on the proximal draw rod component when the draw rod components are positioned in the first position. Rotating the proximal draw rod component relative to the distal draw rod component includes rotating the proximal draw rod component relative to the distal draw rod component so as to align the alignment indicator disposed on the distal draw rod component with a second alignment indicator disposed on the proximal draw rod component.

Sliding the bore of the hollow handle may include sliding the bore of the hollow handle onto the elongated shaft of the proximal draw rod component such that an alignment indicator disposed on the handle is aligned with the alignment indicator disposed on the distal draw rod component.

According to another aspect, a method of assembling a proximal body component of a hip prosthesis to a distal stem component of the hip prosthesis includes sliding a tapered bore of the proximal body component onto a tapered post formed in a superior end of the distal stem component and thereafter positioning a distal tip of a taper assembly instrument into contact with a superior surface of the proximal body component. A threaded end of a draw rod of the taper assembly instrument is threaded into threads formed in the superior end of the distal stem component. The threaded end of the draw rod extends out of the distal tip and is slidable relative thereto. A surgical clamp instrument is secured to the taper assembly instrument. A pair of handles of the surgical clamp instrument are thereafter squeezed so as taper lock the proximal body component and the distal stem component to one another.

The pair of handles of the surgical clamp instrument may be squeezed until a sacrificial tensile bar breaks so as taper lock the proximal body component and the distal stem component to one another.

A pair of clamping jaws of the surgical clamp instrument are positioned onto the draw rod of the taper assembly instrument.

The taper assembly instrument has a handle. A proximal end of the draw rod extends out of a proximal end of the handle and is slideable relative thereto. A knob is secured to the proximal end of the draw rod. Squeezing the pair of handles of the surgical clamp instrument causes the pair of locking jaws to be expanded to move the knob away from the proximal end of the handle.

In an embodiment, a pair of clamping jaws of the surgical clamp instrument are positioned onto the draw rod of the taper assembly instrument. Squeezing the pair of handles of the surgical clamp instrument moves a first clamping jaw of the pair of clamping jaws in a direction away from a second clamping jaw of the pair of clamping jaws.

BRIEF DESCRIPTION OF THE DRAWINGS

The detailed description particularly refers to the following figures, in which.

DETAILED DESCRIPTION OF THE DRAWINGS

Figure 2:
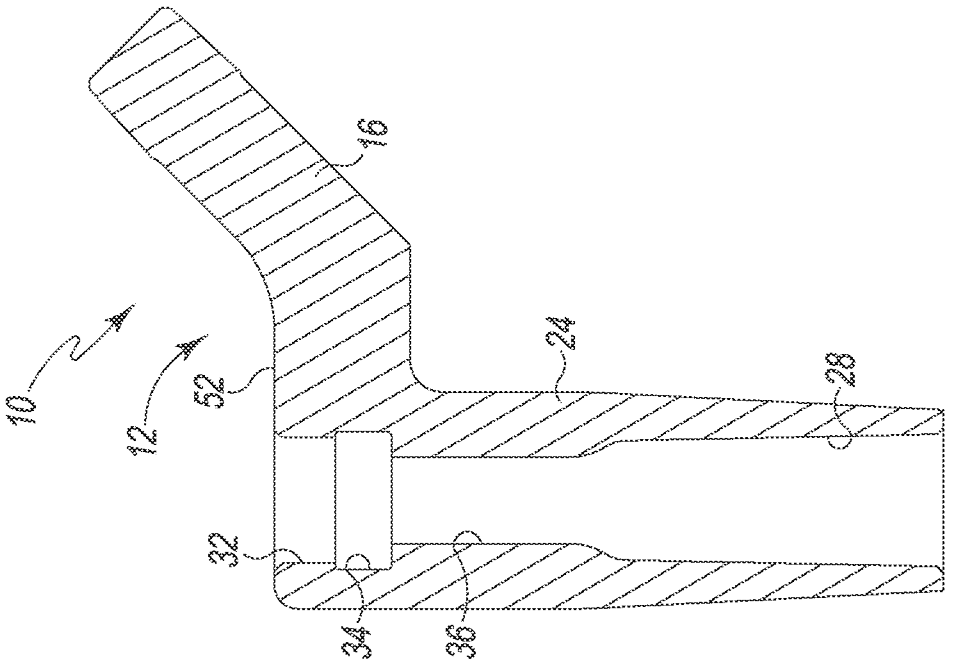
FIG. 2 is cross sectional view of the proximal body component of FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. Additionally, it is to be understood that terms such as top, bottom, front, rear, side, height, length, width, upper, lower, and the like that may be used herein merely describe points of reference and do not necessarily limit embodiments of the present disclosure to any particular orientation or configuration.

Referring now to FIGS. 1-6, there is shown a modular femoral prosthesis 10 for use during performance of a hip replacement procedure. The modular femoral prosthesis 10 includes a proximal body component 12 and a distal stem component 14. The prosthesis 10 is configured to be implanted into a femur of a patient during a hip revision procedure. In particular, the modular prosthesis 10 is implanted into a surgically prepared (e.g. reamed and/or broached) intramedullary canal of the patient's femur.

A head component (not shown) is secured to the end of the elongated neck 16 of the proximal body component 12 to bear on either the patient's natural acetabulum or a prosthetic socket which has been implanted into the patient's pelvis to replace his or her acetabulum. In such a manner, the modular femoral prosthesis 10 and the natural or artificial acetabulum collectively function as a system which replaces the natural joint of the patient's hip.

The distal stem component 14 may be provided in a number of different configurations in order to fit the needs of a given patient's anatomy. In particular, the stem component 14 may be configured in various different lengths to conform to the patient's anatomy (e.g. a relatively long stem component 14 for use with a long femur, a relatively short stem for use with a short femur, etcetera). Moreover, the distal stem component 14 may also be provided in a bow-shaped configuration if required by a given patient's anatomy. Yet further, the distal stem component 14 may also be provided in various diameters if required by a given patient's anatomy. In one illustrative embodiment, the stem component 14 may be provided in four different lengths—140 mm, 190 mm, 240 mm, and 290 mm. Such stem components are provided in 1 mm diameter increments ranging from 14 to 31 mm, although in some embodiments certain of the sizes in such a range (e.g., 28 mm and 30 mm) may be omitted. In such an illustrative embodiment, straight stem components are available in the two shorter lengths (i.e., 140 mm and 190 mm lengths), with the three longer stem lengths (i.e., 190 mm, 240 mm, and 290 mm) being available with a 3-degree angle to accommodate the curvature of the femoral anterior bow.

Likewise, the proximal body component 12 (and the head component secured thereto) may also be provided in various different configurations to provide the flexibility necessary to conform to varying anatomies from patient to patient. For example, the proximal body component 12 may be provided in four different lengths—75 mm, 85 mm, 95 mm, and 105 mm. Like the distal stem component 14, the proximal body component 12 may also be provided in various diameters. For example, in one illustrative embodiment, the proximal body component 12 may be provided in three different diameters—20 mm, 24 mm, and 28 mm. The offset of the proximal body component 12 may be varied to increase the offset of the prosthesis 10. The head component may be provided in varying diameters to fit the needs of a given patient's anatomy.

Figure 1:
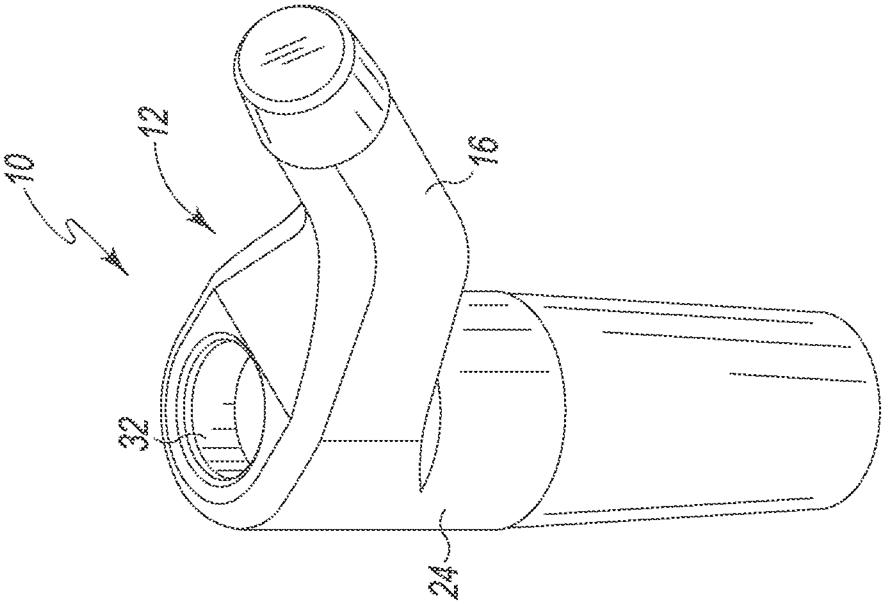
FIG. 1 is a perspective view of a proximal body component of a modular femoral prosthesis for use during performance of a hip revision procedure.

As shown in FIGS. 1 and 2, the proximal body component 12 includes a body 24, with the neck 16 extending medially therefrom. The head component (not shown) is taper fit or otherwise secured to the end of the elongated neck 16. The body 24 also has a tapered bore 28 formed therein. A tapered post 30 of the distal stem component 14 (see FIGS. 3-6) is received into the tapered bore 28 of the proximal body component 12. As will be discussed below in greater detail below, urging the tapered post 30 of the distal stem component 14 and the sidewall defining the tapered bore 28 of the proximal body component 12 toward one another taper locks the proximal body component 12 to the distal stem component 14.

The superior surface 52 of the body 24 of the proximal body component 12 has a countersunk cavity 32 formed therein. The inferior side of the countersunk cavity 32 opens into a locking recess 34. The inferior side of the locking recess 34 opens into a connecting bore 36, which in turn opens into the tapered bore 28. As will be discussed below in greater detail, a taper assembly instrument is inserted through the countersunk cavity 32 and thereafter extends through the connecting bore 36 to engage the distal stem component 14.

As shown in FIGS. 3-6, the tapered post 30 is formed in the superior end of the body 38 of the distal stem component 14. The superior surface of the body 38 of the distal stem component 14 has a set of upper threads 40 formed therein. As will be discussed below in more detail, the upper threads 40 are used to couple the distal stem component 14 to surgical instruments during use thereof. A set of lower threads 42 are positioned inferiorly of the upper threads 40. The lower threads 42 are used to couple the distal stem component 14 to a locking bolt (not shown) of the hip prosthesis 10. By not subjecting the lower threads to impacted surgical instruments during implantation of the femoral prosthesis 10, the threads ultimately used to secure the prosthesis's bolt (i.e., the lower threads 42) are protected from damage during the surgical procedure. In the exemplary embodiment described herein, the upper threads 40 are M8 size threads, whereas the lower threads 42 are M6 size threads.

In the illustrative embodiment described herein, the lower threads 42 are embodied as modified threads designed to relieve stress risers. In particular, as can be seen best in FIG. 6, the outer edges 54 of the lower threads 42 are rounded. Unexpectedly, testing and modeling have shown that such rounded edges 54 provide relief from stress risers in the distal stem component 14. Additional relief from stress risers is also provided by the design of the distal end of the blind hole in which the lower threads 42 are formed. In particular, in lieu of a point or other geometry, the distal end 56 of the blind hole extending posteriorly from the lower threads 42 is rounded. That is, the blind hole formed in the body 38 of the distal stem component 14 that extends posteriorly from the threads 42 has a rounded distal end 56. Like the rounded outer edges 54 of the lower threads 42, testing and modeling have unexpectedly shown that such a rounded distal end 56 provides relief from stress risers in the distal stem component 14.

An alignment key 44 in the form of, for example, a tab extends superiorly from the superior surface of the body 38 of the distal stem component 14. The alignment key 44 is in line with the apex of the distal stem component 14. That is, bowed stem components 14 have an apex (i.e., a spine) that runs along the convex side of its curvature. During implantation of the distal stem component 14, the apex must be properly aligned with the corresponding side of the patient's femur possessing a similar curvature. As will be described below, the alignment key 44 facilitates proper orientation of the apex of the distal stem component 14 by allowing the surgeon to visualize the location of the apex even when the stem component 14 is positioned in the intramedullary canal.

Figures 3, 4, 5, 6:
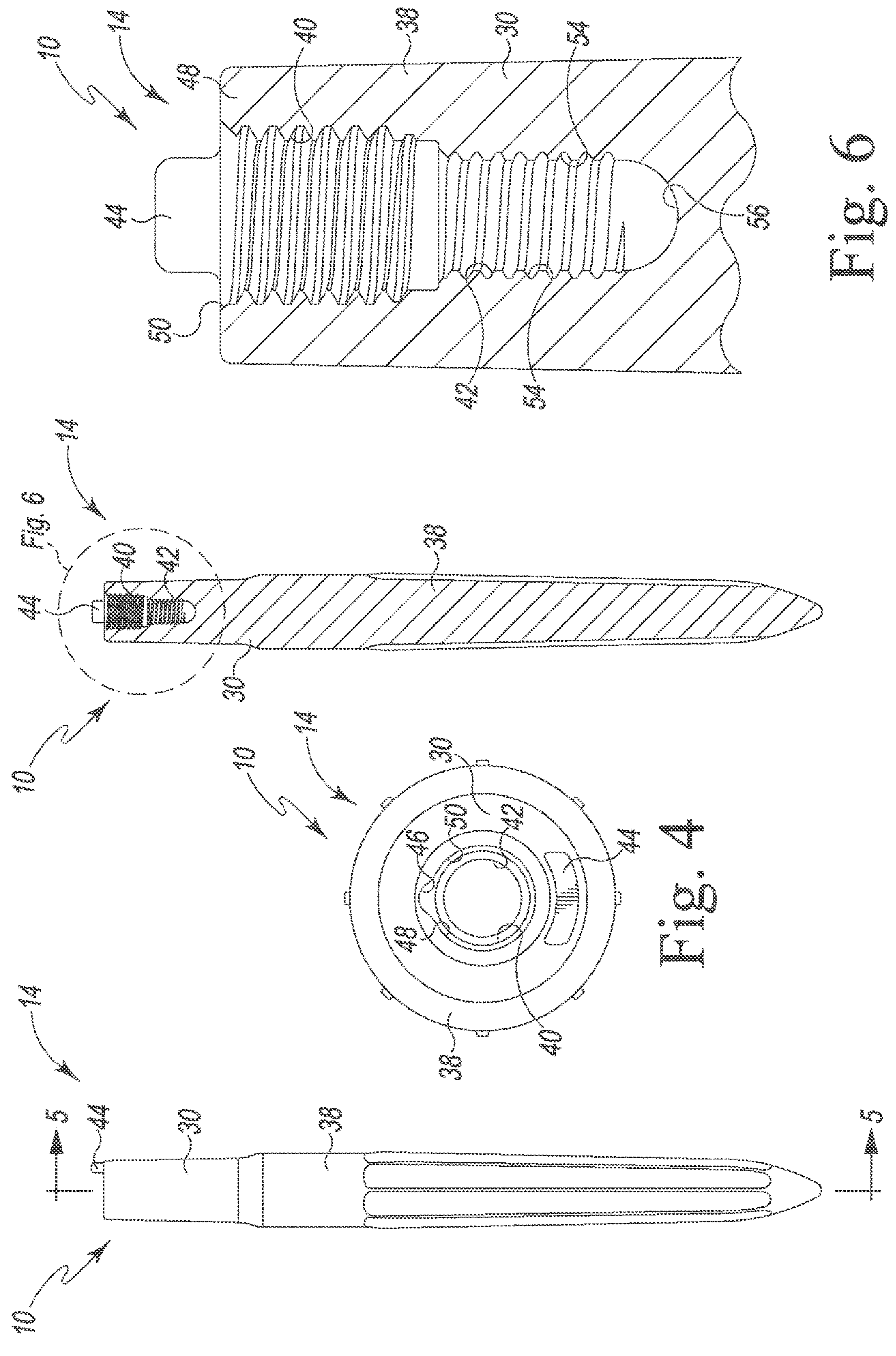
FIG. 3 is an elevation view of a distal stem component of a modular femoral prosthesis for use along with the proximal body component during performance of a hip revision procedure.
FIG. 4 is a top elevation view of the distal stem component of FIG. 3.
FIG. 5 is a cross sectional view of the distal stem component taken along the line 5-5 of FIG. 3, as viewed in the direction of the arrows.
FIG. 6 is an enlarged fragmentary cross sectional view showing the distal stem component in greater detail, with FIG. 6 being taken from FIG. 5 as indicated by the encircled area.

As can be seen in FIG. 4, a keyway 46 is formed in the superior surface of the body 38 of the distal stem component 14. The keyway 46 is formed in the sidewall 48 that defines the outer opening 50 of the upper threads 40. In the exemplary embodiment described herein, the keyway 46 is embodied as a lobe-shaped slot configured to receive a lobe-shaped key of a surgical trial instrument, although other shaped slots and tabs may be used.

Figure 7:
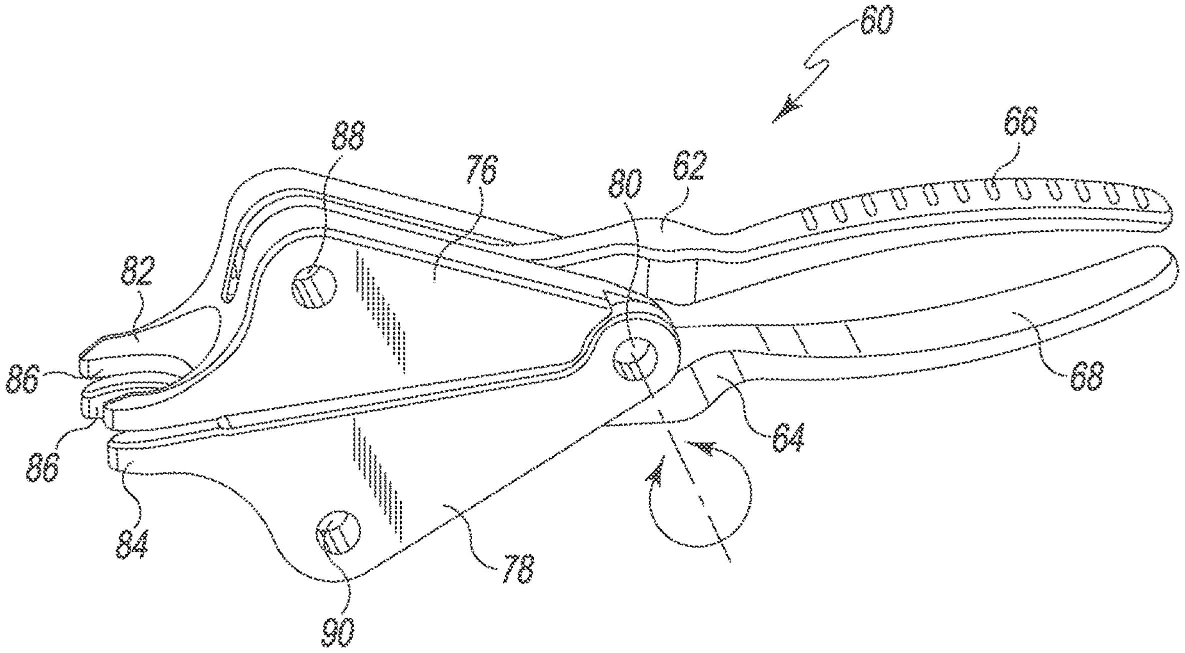
FIG. 7 is a perspective view of an orthopaedic clamp instrument that is operable to taper lock the proximal body component of FIG. 1 and the distal stem component of FIG. 3 to one another.

Referring now to FIGS. 7-31, some examples of instruments used to taper lock the components of the femoral prosthesis 10 are shown. In FIG. 7, there is shown an orthopaedic surgical clamp instrument 60. The clamp instrument 60 is used in conjunction with an orthopaedic taper assembly instrument 150 (see FIGS. 15-29) to apply a mechanical load on the proximal body component 12 and the distal stem component 14 to taper lock them to one another. The clamp instrument 60 is lighter and more compact relative to prior devices and advantageously increases force multipliers for a large range of user input force capabilities.

Figure 8:
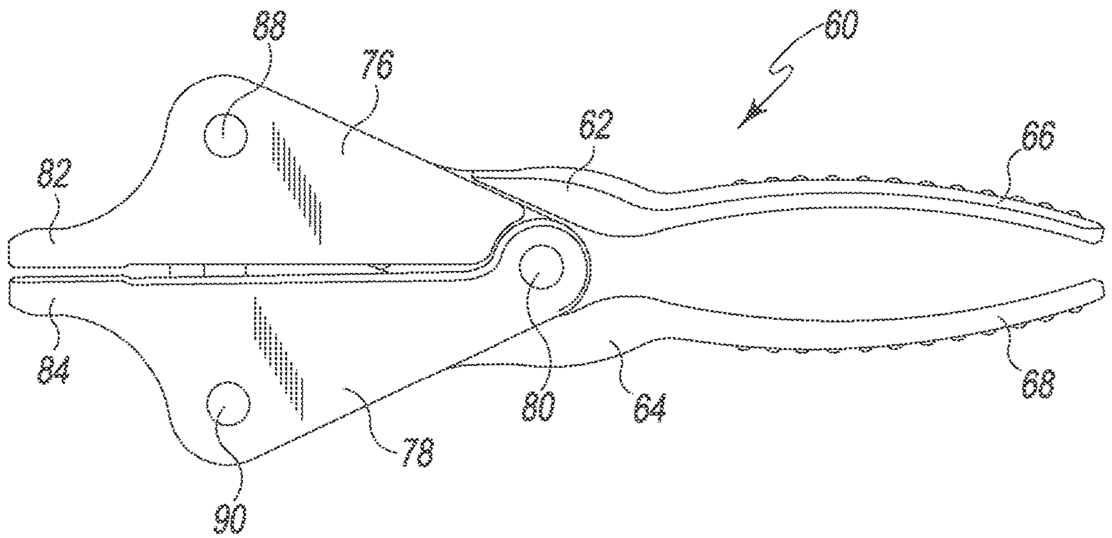
FIG. 8 is a side elevation view of the clamp instrument of FIG. 7.
Figure 9:
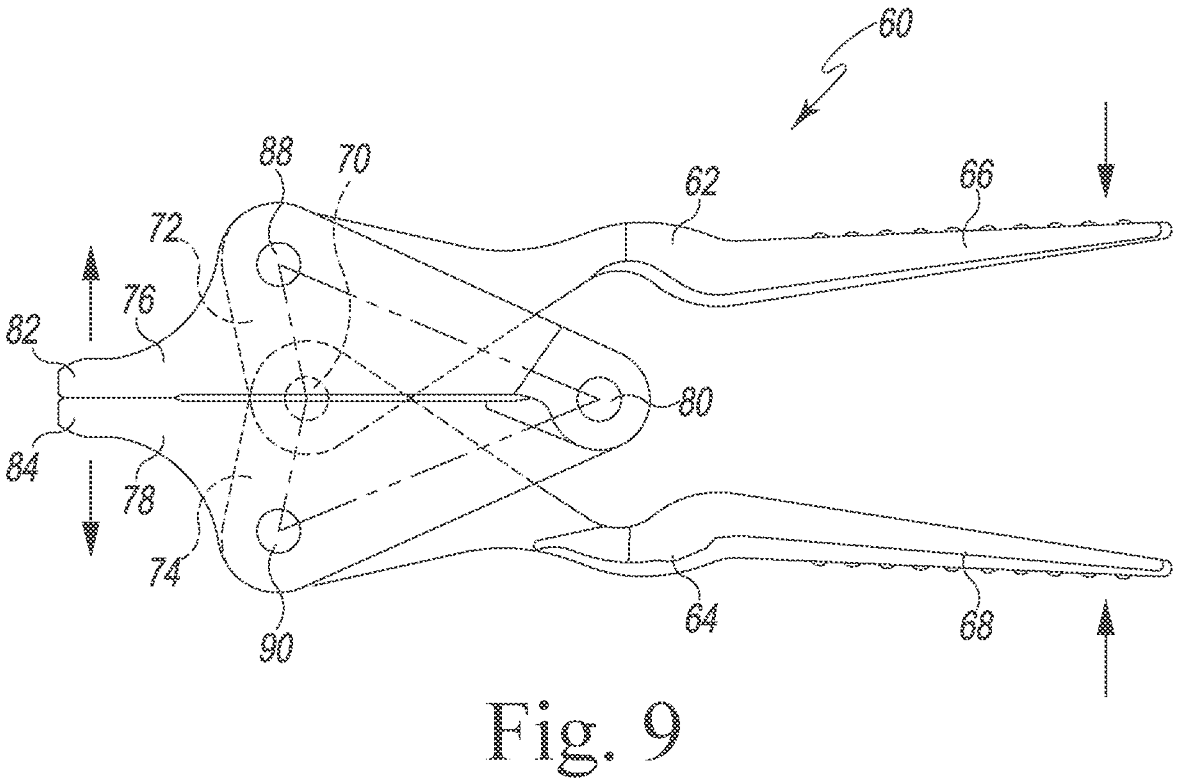
FIGS. 9 and 10 are views similar to FIG. 8, but showing internal features of the clamp instrument in dashed lines.
Figure 10:
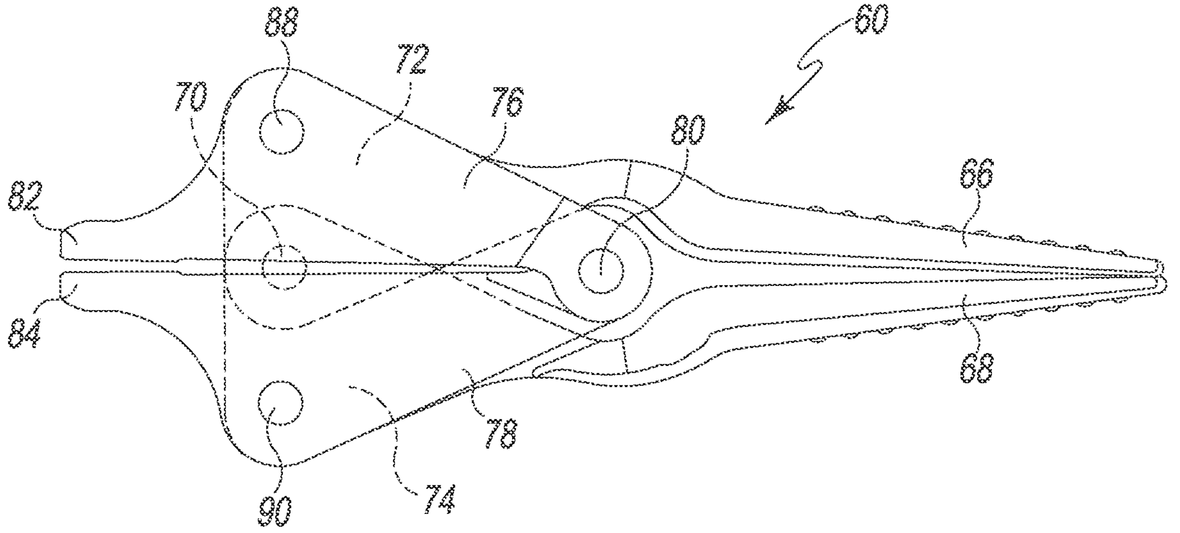
Figure 11:
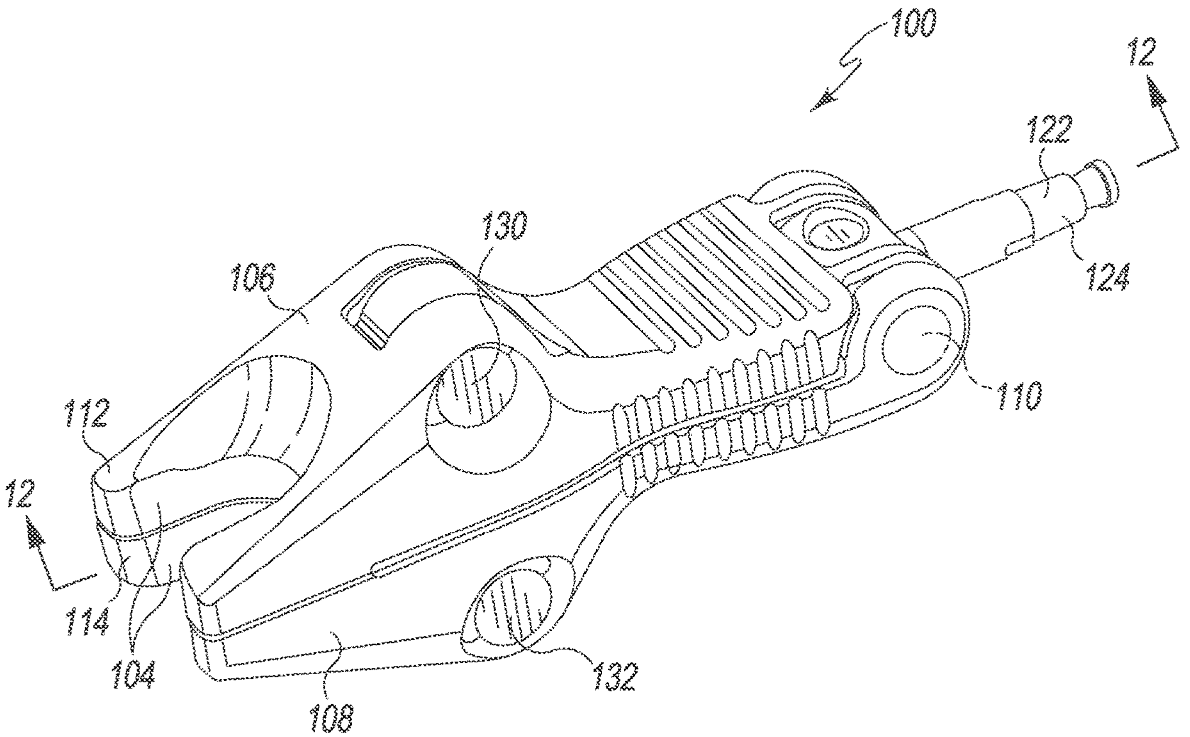
FIG. 11 is a perspective view of another embodiment of an orthopaedic clamp instrument that is operable to taper lock the proximal body component of FIG. 1 and the distal stem component of FIG. 3 to one another.

A can be seen in FIGS. 7 and 8, the clamp instrument 60 includes a pair of levers 62, 64. A proximal end of each of the levers 62, 64 includes a handle 66, 68, respectively. The handles 66, 68 have a ribbed or similarly textured outer surface. Such a textured surface increases the surgeon's ability to grip the handles 66, 68, particularly in the presence of the fluids commonly present during a surgical procedure. The opposite, distal end of the levers 62, 64 includes a pivot flange link 72, 74, respectively. As can be seen in FIGS. 9 and 10, the upper end of the pivot flange link 74 of the lever 64 is pivotally coupled to the lower end of the pivot flange link 72 of the lever 62 at a pivot joint 70. Thus, the two levers 62, 64 pivot about the pivot joint 70 as the handles 66, 68 are squeezed (or released) by a user.

The clamp instrument 60 also includes a pair of clamping jaws 76, 78. As can be seen in FIGS. 7-10, each of the clamping jaws 76, 78 has a socket 82, 84, respectively, formed in its distal end. As will be discussed below in more detail, the sockets 82, 84 are configured to receive the draw rod of the taper assembly instrument 150. In the illustrative embodiment described herein, the sockets 82, 84 include a generally U-shaped opening 86 into which the draw rod is positioned during use of the clamp instrument 60.

As can be seen in FIGS. 7-10, the proximal ends of the clamping jaws 76, 78 are pivotally coupled to one another at a pivot joint 80. As will be described below, the two clamping jaws 76, 78 pivot about the pivot joint 80 as the handles 66, 68 are squeezed (or released) by a user. As can best be seen in FIGS. 9 and 10, the upper end of the upper clamping jaw 76 is pivotally coupled to the upper end of the pivot flange link 72 of the lever 62 at a pivot joint 88, whereas the lower end of the lower clamping jaw 78 is pivotally coupled to the lower end of the pivot flange link 74 of the lever 64 at a pivot joint 90. Such an arrangement allows the clamping jaws 76, 78 to pivot about the levers 62, 64, respectively, as the handles 66, 68 are squeezed (or released) by a user thereby allowing the sockets 82, 84 to be moved relative to one another. In particular, as can be seen in FIGS. 9 and 10 when a surgeon or other user squeezes the handles 66, 68 (i.e., moves them towards one another), the pivot flange links 72, 74 pivot about the pivot joint 70 which urges the pivot joint 70 distally away from the proximal ends of the clamping jaws 76, 78 (and hence the pivot joint 80) thereby causing the proximal ends of the clamping jaws 76, 78 to pivot about pivot joint 80. Similarly, as the pivot flange links 72, 74 pivot about the pivot joint 70, the lower end of the lower pivot flange link 74 of the lever 64 (and hence the pivot joint 90) and the upper end of the upper pivot flange link 72 of the lever 62 (and hence the pivot joint 88) are moved away from one another. Such movement of the of the pivot joints 88, 90 away from one another causes the sockets 82, 84 to be urged or otherwise moved away from one another.

Oppositely, when a surgeon or other user releases the handles 66, 68 (i.e., moves them away one another), the pivot flange links 72, 74 pivot about the pivot joint 70 which urges the pivot joint 70 proximally toward the proximal ends of the clamping jaws 76, 78 (and hence the pivot joint 80) thereby causing the proximal ends of the clamping jaws 76, 78 to pivot about pivot joint 80. Similarly, as the pivot flange links 72, 74 pivot about the pivot joint 70, the lower end of the lower pivot flange link 74 of the lever 64 (and hence the pivot joint 90) and the upper end of the upper pivot flange link 72 of the lever 62 (and hence the pivot joint 88) are moved toward one another. Such movement of the of the pivot joints 88, 90 toward one another causes the sockets 82, 84 to be urged or otherwise moved toward one another.

As can be seen in the phantom lines connecting the pivot joints 70,80, 88, 90 in FIG. 9, the arrangement of the pivot flange links 72, 74 and clamping jaw 76, 78, including the locations of pivot joints 70, 80, 88, 90, defines a four-bar linkage. Such an arrangement provides mechanical efficiency and reliability of operation.

Referring now to FIGS. 11-14, there is shown another embodiment of a clamp instrument 100. The clamp instrument 100 functions similarly to the clamp instrument 60 except that it is configured for mechanical input from a rotary tool (e.g., powered driver) instead of manual input from the handles 66, 68.

Like the manual clamp instrument 60, the clamp instrument 100 includes a pair of clamping jaws 106, 108. As can be seen in FIGS. 7-10, each of the clamping jaws 106, 108 has a socket 112, 114, respectively, formed in its distal end. As will be discussed below in more detail, the sockets 112, 114 are configured to receive the draw rod of the taper assembly instrument 150. In the illustrative embodiment described herein, the sockets 112, 114 include a generally U-shaped opening 104 into which the draw rod is positioned during use of the clamp instrument 100. As can be seen in FIGS. 11-14, the proximal ends of the clamping jaws 106, 108 are pivotally coupled to one another at a pivot joint 110. As will be described below, the two clamping jaws 106, 108 pivot about the pivot joint 110 when rotary motion is input by a user.

Figure 12:
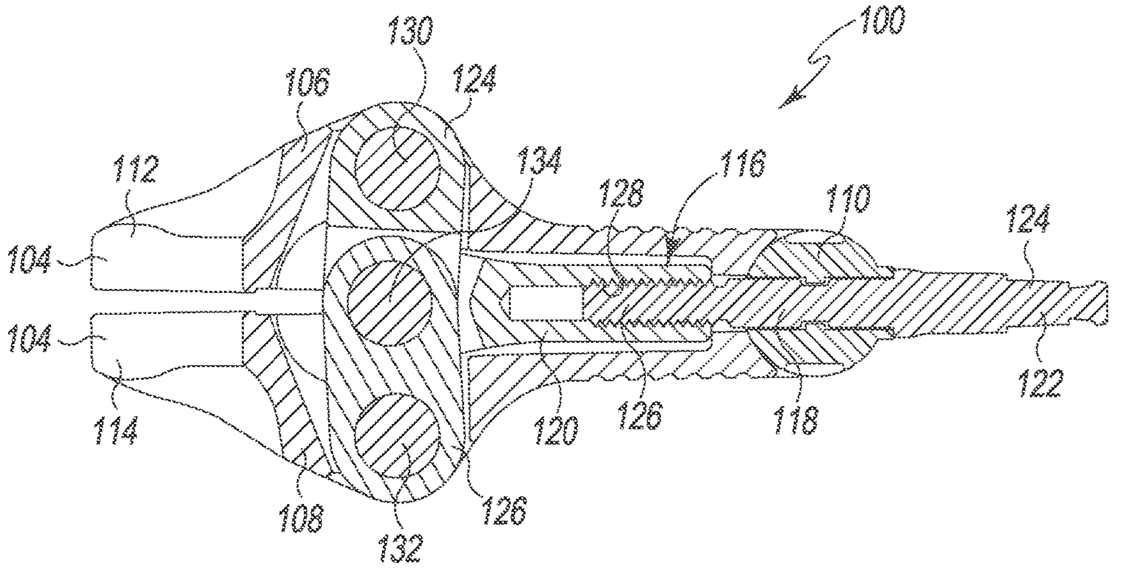
FIG. 12 is a cross sectional view of the clamp instrument of FIG. 11, taken along the line 12-12 of FIG. 11, as viewed in the direction of the arrows.

As shown best in FIG. 12, a threaded drive assembly 116 is operatively coupled to the clamping jaws 106, 108 and is operable to move the clamping jaws 106, 108 (and hence the sockets 112, 114) toward and away from one another. Specifically, the threaded drive assembly 116 includes a drive screw 118 and a drive link 120. The drive screw 118 is rotatably coupled to the proximal ends of the clamping jaws 106, 108 and includes a connector 122 configured to be secured to a rotary tool defined in its proximal end 124. A threaded shaft 126 extends distally away from the connector 122. The drive link 120 is slidably coupled to the clamping jaws 106, 108 so as to be movable within the clamping jaws 106, 108 in a direction toward, and a direction away from, the sockets 112, 114. The drive link 120 has a threaded bore 128 formed therein. The threaded shaft 126 of the drive screw 118 is threadingly received into the threaded bore 128 of the drive link 120. Rotation of the threaded shaft 126 of the drive screw 118 within the threaded bore 128 of the drive link 120 causes linear movement of the drive link 120 within the clamping jaws 106, 108.

As can be seen in FIGS. 11-14, the connector 122 is configured to be received into the chuck of a manual or powered driver (not shown). When a surgeon or other personnel rotates the drive screw 118, the drive screw's threaded shaft 116 is likewise rotated thereby causing linear movement of the drive link 110. Rotation in one direction (e.g., clockwise) moves the drive link 110 in the direction away from the sockets 112, 114 of the clamping jaws 106, 108 thereby moving the sockets 112, 114 of the clamping jaws 106, 108 away from one another. Rotation in the opposite direction (e.g., counterclockwise) moves the drive link 110 in the direction toward the sockets 112, 114 of the clamping jaws 106, 108 thereby moving the sockets 112, 114 of the clamping jaws 106, 108 toward one another.

Figure 13:
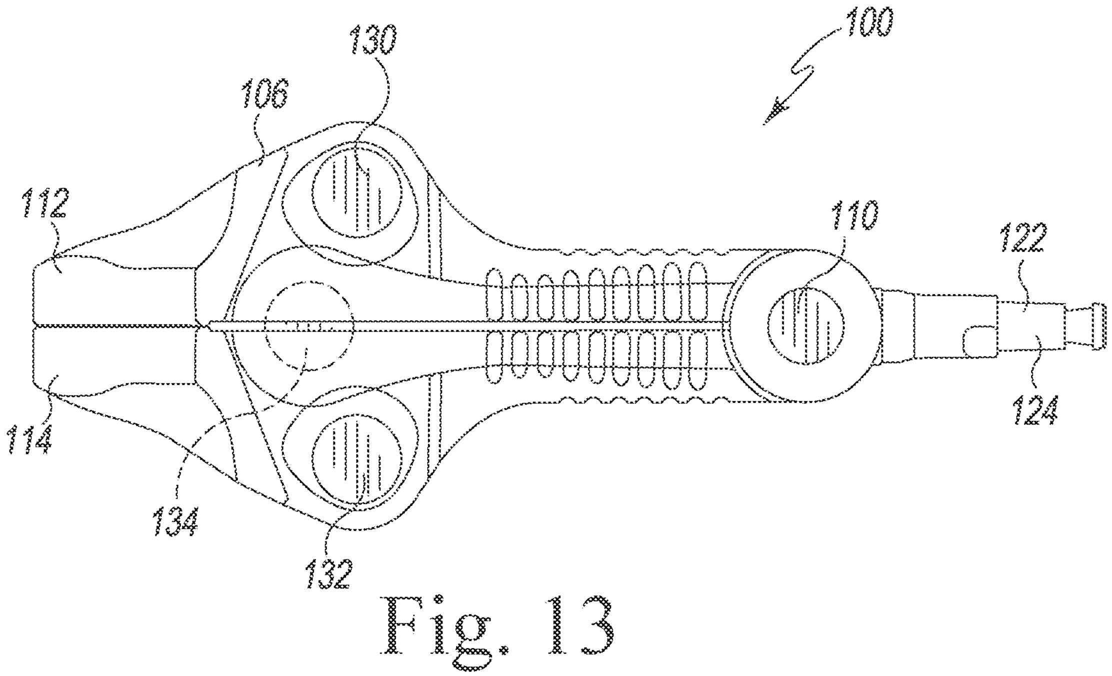
FIGS. 13 and 14 are side elevation views of the clamp instrument of FIG. 11, note some internal features of the clamp instrument are shown in dashed lines.
Figure 14:
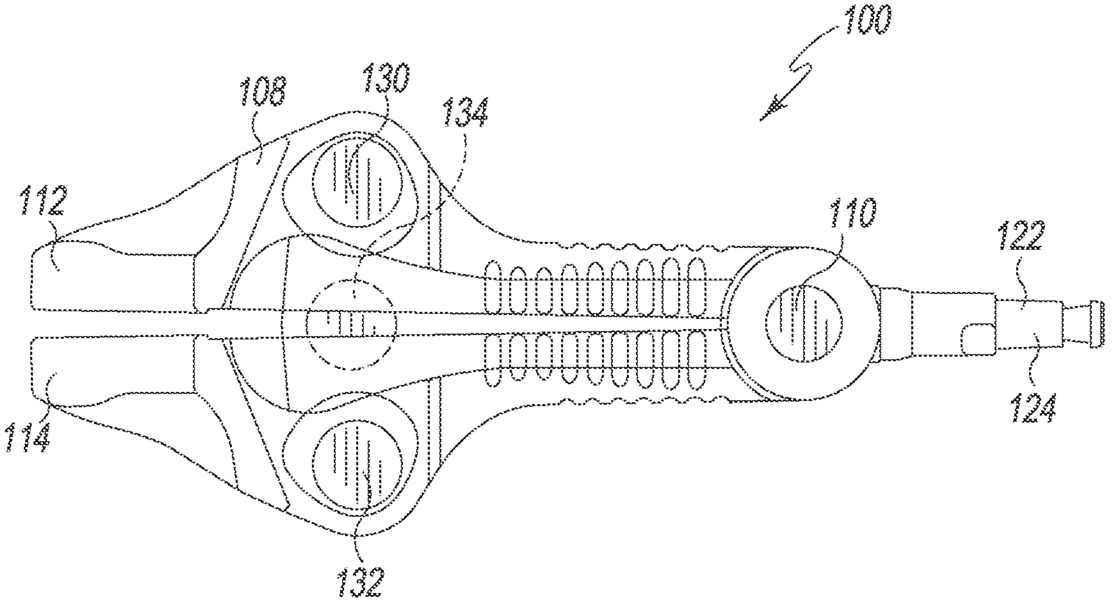
Figure 15:
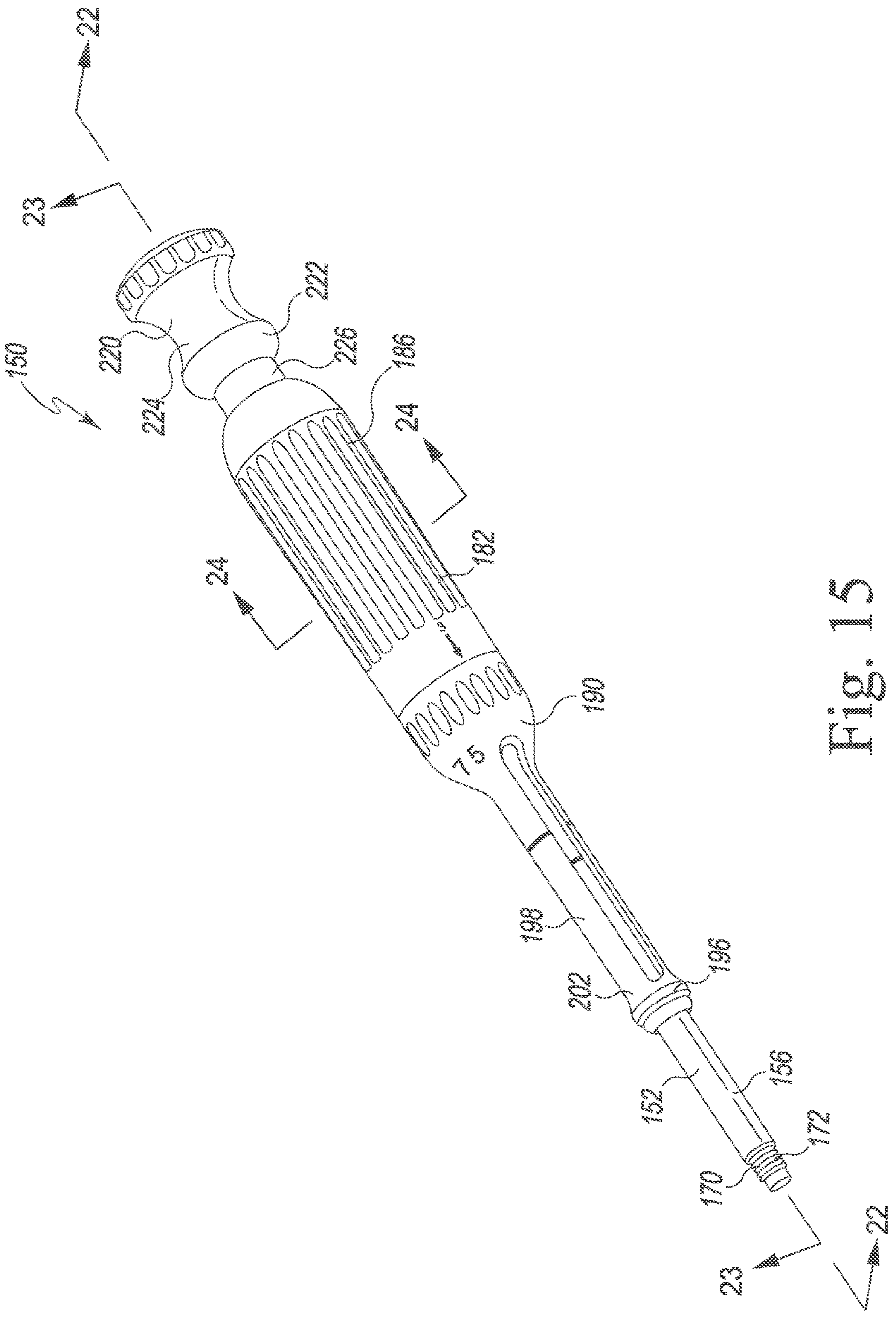
FIG. 15 is a perspective view of a taper assembly instrument that is operable to taper lock the proximal body component of FIG. 1 and the distal stem component of FIG. 3 to one another.

As can be seen in FIGS. 12-14, the drive link 110 is coupled to the clamping jaws 106, 108 by a pair of connecting links 124, 126, respectively. In particular, the distal end of the drive link 110 is pivotally coupled to the lower end of the connecting link 124 at a pivot joint 134, with the connecting link's opposite upper end being coupled to the clamping jaw 106 at a pivot joint 130. Similarly, the distal end of the drive link 110 is pivotally coupled to the upper end of the connecting link 126 at the pivot joint 134, with the connecting link's opposite lower end being coupled to the clamping jaw 108 at a pivot joint 132. As the drive link 110 is driven within the clamping jaw 106, 108 in a direction toward, and a direction away from, the sockets 112, 114, the pivot joint 134 translates within the clamping jaws in a similar direction. In particular, rotation of the connector 122 (and hence the drive screw's threaded shaft 116) in one direction (e.g., clockwise) moves the drive link 110 (and hence the pivot joint 134) in the direction away from the sockets 112, 114 of the clamping jaws 106, 108 thereby moving the pivot joints 130, 132 (and hence the sockets 112, 114 of the clamping jaws 106, 108) away from one another. Rotation of the connector 122 (and hence the drive screw's threaded shaft 116) in the opposite direction (e.g., counter-clockwise) moves the drive link 110 (and hence the pivot joint 134) in the direction toward the sockets 112, 114 of the clamping jaws 106, 108 thereby moving the pivot joints 130, 132 (and hence the sockets 112, 114 of the clamping jaws 106, 108) toward one another.

Referring now to FIGS. 15-29, there is shown an orthopaedic taper assembly instrument 150 that may be used with either of the clamp instruments 60, 100 to apply a mechanical load on the proximal body component 12 and the distal stem component 14 to taper lock them to one another. The taper assembly instrument 150 is simpler and slimmer relative to prior devices and advantageously is easier to assemble and use.

The taper assembly instrument 150 includes a draw rod 152 that includes two draw rod components 154, 156. The proximal draw rod component 154 includes an elongated shaft 158 that has a set of threads 160 formed in its proximal end 162. A tensile bar slot 164 is formed in the opposite, distal end 166 of the elongated shaft 158. Similarly, the distal draw rod component 156 includes an elongated shaft 168 that has a set of threads 170 formed in its distal end 172. A tensile bar slot 174 is formed in the opposite, proximal end 176 of the elongated shaft 168. As can be seen in FIGS. 17-21, when the distal end 166 of the elongated shaft 158 is abutted with the proximal end 176 of the elongated shaft 168, the tensile bar slots 164, 174 cooperate to cavity 178 into which a sacrificial tensile bar component 180 is received.

Figure 25:
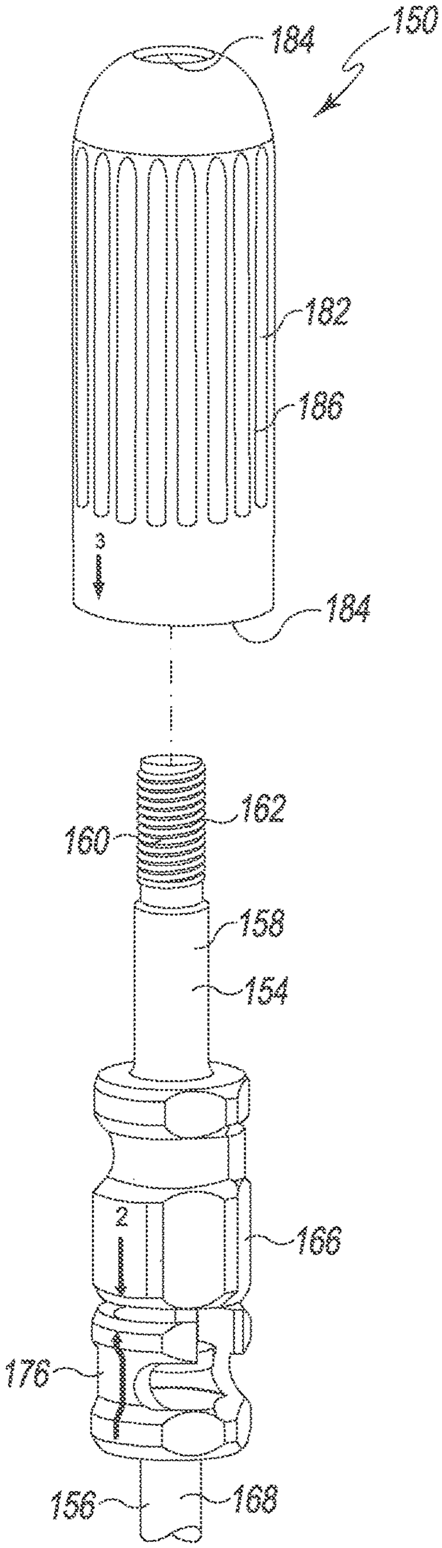
FIGS. 25-27 are enlarged, fragmentary views showing the handle being installed on the draw rod of the taper assembly instrument of FIG. 15.

The taper assembly instrument 150 also includes a removable handle 182. The handle 182 is embodied as a hollow elongated structure and, as such, has an elongated bore 184 extending through its body. The handle 182 may be installed on the elongated shaft 158 of the proximal draw rod component 154 by inserting the proximal end 162 of the shaft 158 into the distal end of the handle's bore 184 (as shown in FIG. 25) and thereafter advancing the shaft 158 within the bore 184 until its threaded proximal end 162 exits the proximal end of the bore 184. The handle 182 also includes an elongated outer surface 186 that extends parallel to the handle's bore 184 and is configured to be gripped during use of the taper assembly instrument 150. The outer surface 186 of the handle 182 has a ribbed or similarly textured outer surface. Such a textured surface increases the surgeon's ability to grip the handle 182, particularly in the presence of the fluids commonly present during a surgical procedure.

Figure 28:
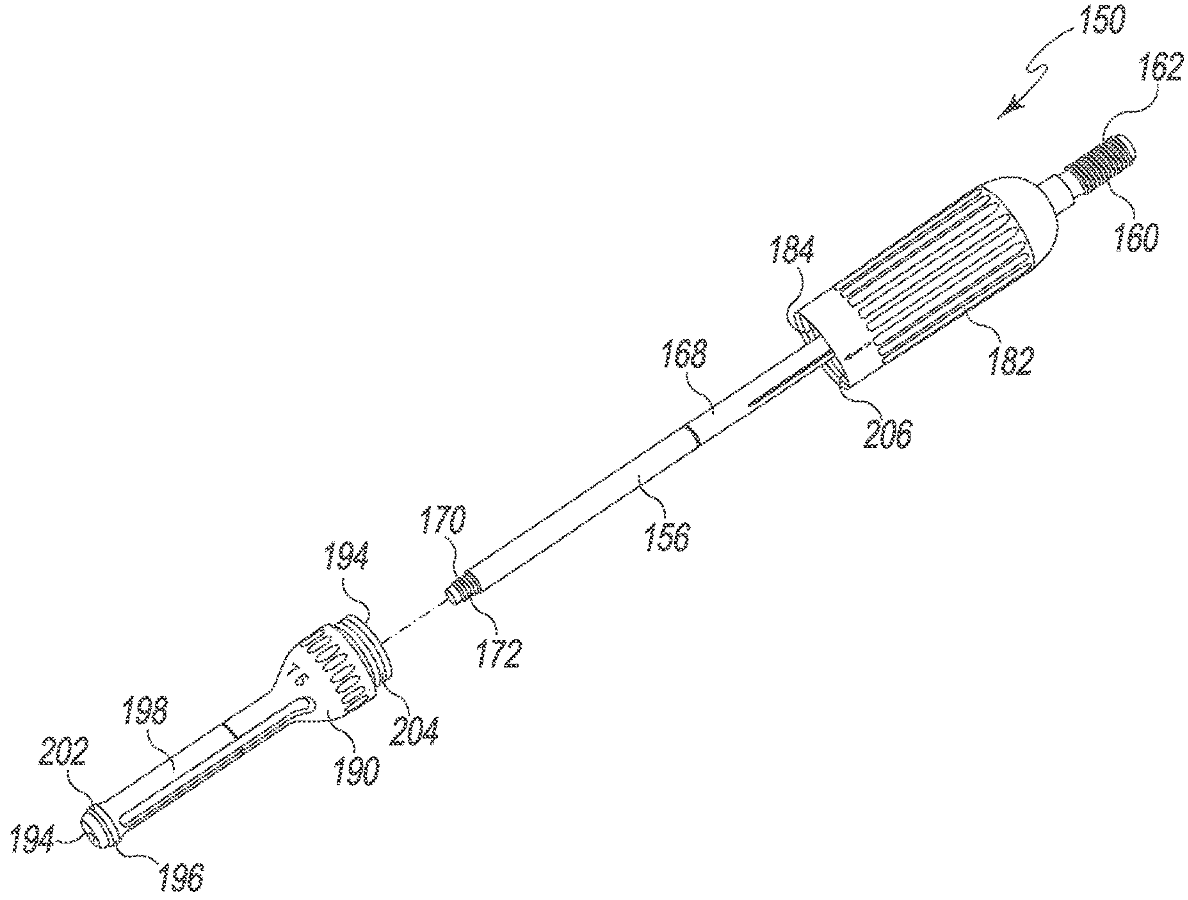
FIGS. 28 and 29 are perspective views showing the tip component being installed on the handle of the taper assembly instrument of FIG. 15.

The taper assembly instrument 150 also includes a removable tip component 190. The tip component 190 is embodied as a hollow elongated structure and, as such, has an elongated bore 194 extending through its body. The tip component 190 may be installed on the elongated shaft 168 of the distal draw rod component 156 by inserting the distal end 172 of the shaft 168 into the proximal end of the tip component's bore 194 (as shown in FIG. 28) and thereafter advancing the shaft 168 within the bore 194 until its threaded distal end 172 exits the distal end of the bore 194. The tip component 190 has an annularly-shaped shoulder 196 that extends outwardly from its outer surface 198 near the component's distal end 202. As will be discussed below, the shoulder 196 has a diameter that is larger than the diameter of the countersunk cavity 32 formed in the superior surface 52 of the body 24 of the proximal body component 12 (see FIGS. 1 and 2). As such, the shoulder 196 functions as a stop that prevents the tip component 190 from being fully received into the countersunk cavity 32.

Figure 16:
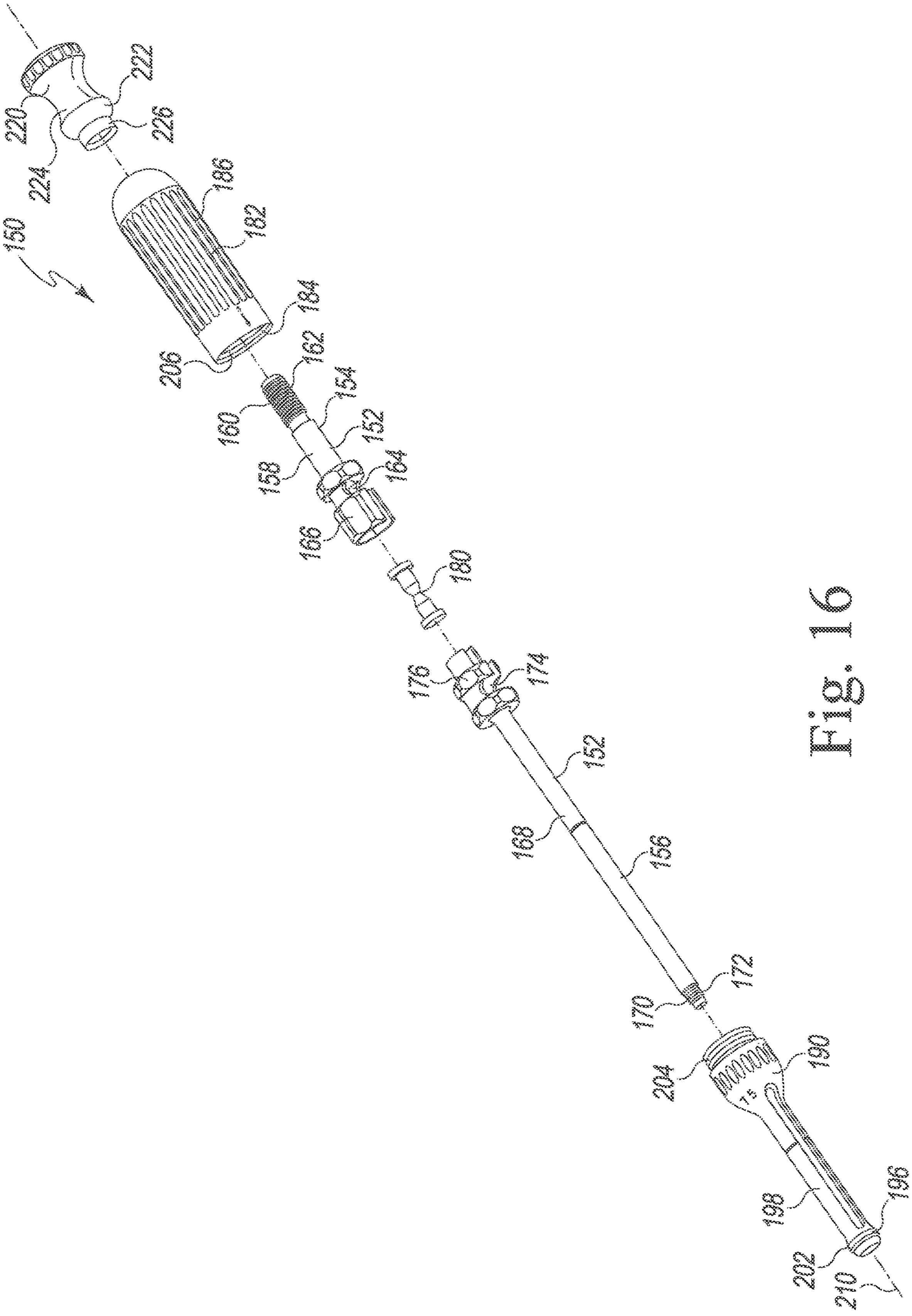
FIG. 16 is an exploded perspective view of the taper assembly instrument of FIG. 15.
Figure 17:
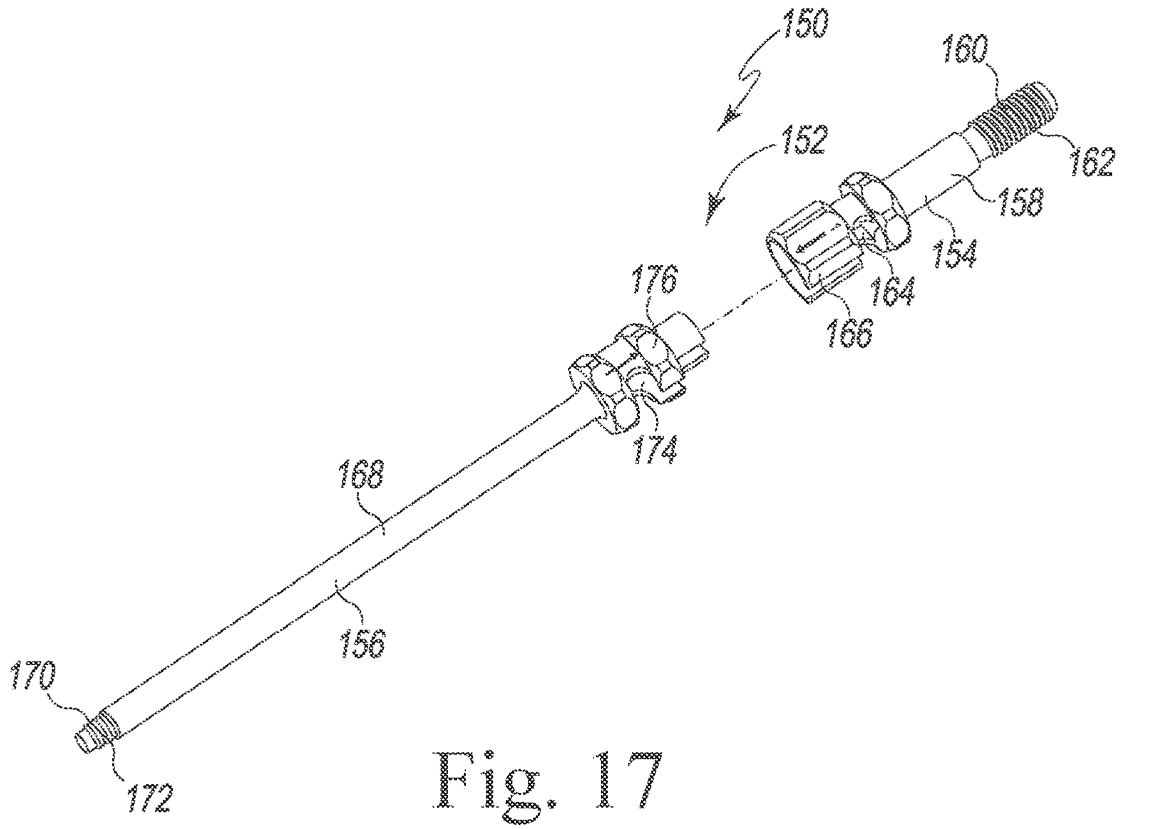
FIG. 17 is an exploded perspective view of the draw rod components of the taper assembly instrument of FIG. 15.
Figure 18:
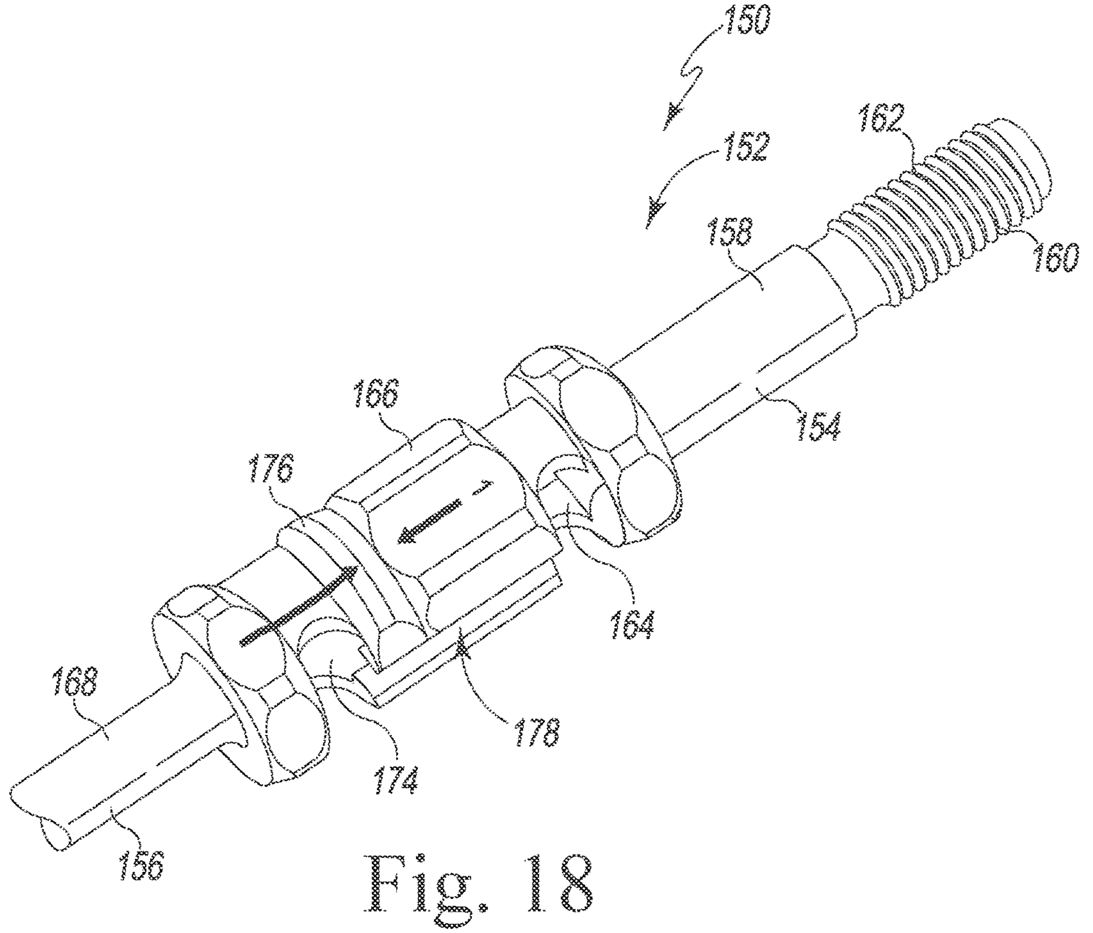
FIG. 18 is an enlarged, fragmentary view showing the draw rod components of FIG. 17 aligned and abutting one another.

As can be seen in FIG. 16, the tip component 190 has a set of threads 204 formed in its proximal end. Similarly, the handle 182 has a set of threads 206 formed in its distal end. The threads 204, 206 allow the tip component 190 to be removably screwed onto the handle 182. In doing so, the draw rod 152 may be captured in the assembly of the handle 182 and tip component 190. When so captured, the draw rod 152 freely slides back and forth with the assembly of the handle 182 and tip component 190.

As shown in FIGS. 15, 16, 22, and 23, the assembled components of the taper assembly instrument 150 lie on a common axis 210. In particular, the longitudinal axis of each of the elongated shafts 158, 168 of the draw rod components 154, 156, the elongated bore 184 of the handle, and the elongated bore 194 of the tip component 190 are all collinear with one another. In other words, a common longitudinal axis 210 pass through the longitudinal axis of each of the elongated shafts 158, 168 of the draw rod components 154, 156, the elongated bore 184 of the handle, and the elongated bore 194 of the tip component 190. When the instrument is fully assembled, the tensile bar component 180 and the knob 220 secured to the threads 160 on the proximal end of the draw rod 152 also lie on the share the common longitudinal axis 210.

As alluded to above, the taper assembly instrument 150 includes a knob 220 secured to the threads 160 on the proximal end 162 of the draw rod's proximal draw rod component 154. As can best be seen in FIGS. 16, 22, and 23, the knob 220 has an annularly-shaped shoulder 222 that extends outwardly from its outer surface 224 near the knob's distal end 226. As will be discussed below, the shoulder 222 functions as abutment surface against which the clamping jaws of the clamp instrument may bear to move the knob 220 (and hence the draw rod 152) relative to the assembly of the handle 182 and the tip component 190.

Figure 19:
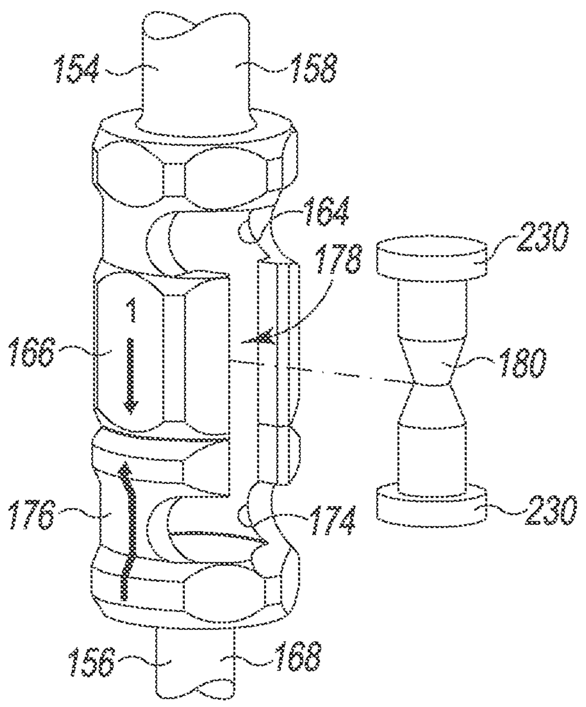
FIGS. 19 and 20 are fragmentary perspective views showing the tensile bar component being loaded into the draw rod of the taper assembly instrument of FIG. 15.
Figures 22, 23:
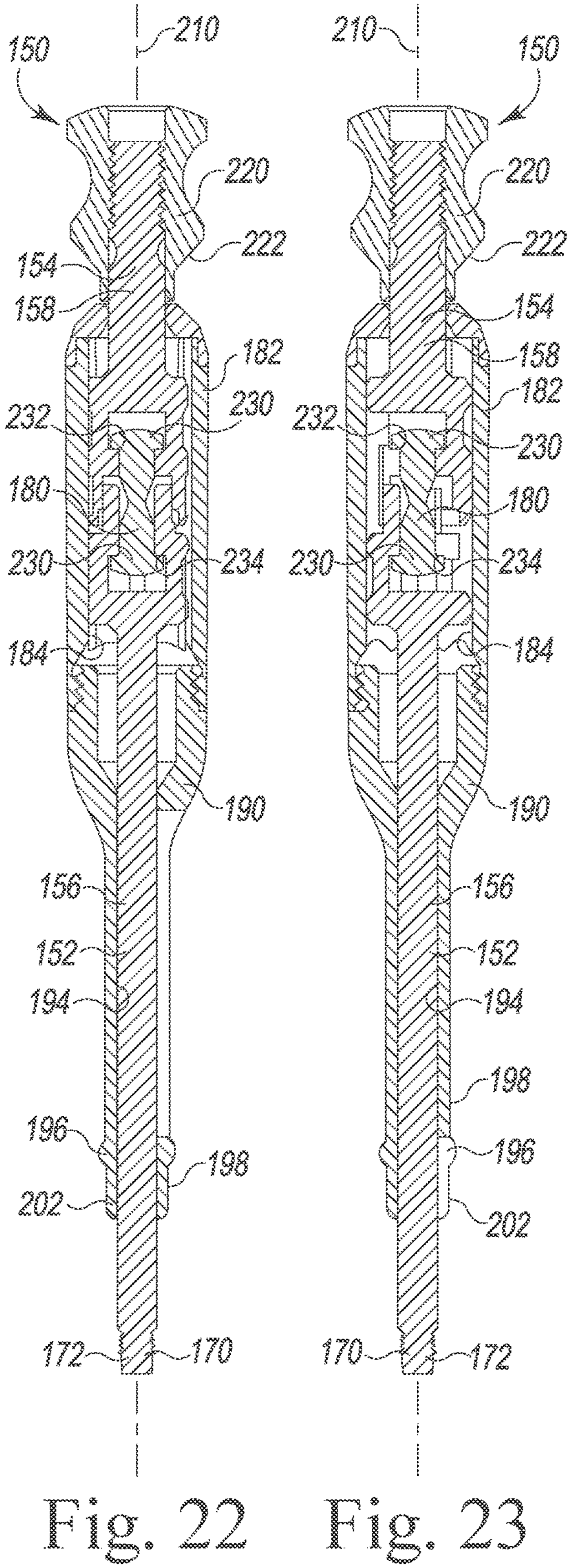
FIG. 22 is a cross sectional view of the taper assembly instrument taken along the line 22-22 of FIG. 15, as viewed in the direction of the arrows.
FIG. 23 is a cross sectional view of the taper assembly instrument taken along the line 23-23 of FIG. 15, as viewed in the direction of the arrows.
Figure 24:
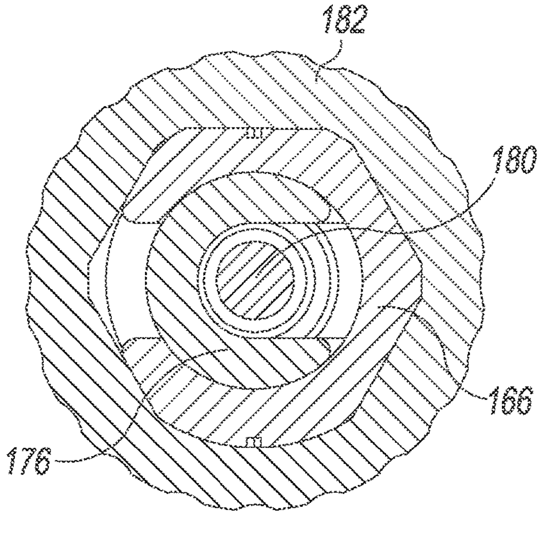
FIG. 24 is a cross sectional view of the taper assembly instrument taken along the line 24-24 of FIG. 15, as viewed in the direction of the arrows.

The taper assembly instrument 150 is operable to deliver a predetermined mechanical load on the proximal body component 12 and the distal stem component 14 to taper lock them to one another. The sacrificial tensile bar component 180 is utilized to ensure the predetermined load is delivered, but not exceeded. The tensile bar component 180 is configured to break when an axial force representing the predetermined load is applied to it. As can be seen in FIGS. 19, 22, and 23, the tensile bar component 180 has a generally hour-glass shape with an annular flange 230 formed in each of its ends. The flanges 230 function as shoulders which abut shoulders formed in the ends of the draw rod components 154, 156. Specifically, the distal end 166 of the elongated shaft 158 of the proximal draw rod component 154 has a collar 232 formed therein at location within its tensile bar slot 164. Similarly, the proximal end 176 of the elongated shaft 168 of the distal draw rod component 156 has a collar 234 formed therein at location within its tensile bar slot 174. As can be seen in FIGS. 22 and 23, when the tensile bar component 180 is loaded into the cavity 178 created by the tensile bar slots 164, 174, tensile bar component 180 is clamped between the collars 232, 234. Specifically, the lower surface of the annular flange 230 on the upper end of the tensile bar component 180 abuts the upper surface of the collar 232 and the upper surface of the annular flange 230 on the lower end of the tensile bar component 180 abuts the lower surface of the collar 234.

As will be described in more detail below, during use of the taper assembly instrument 150, the tensile bar component 180 clamped between the collars 232, 234 of the draw bar components 152, 154 is the mechanical linkage that couples the draw bar components 152, 154 to one another. As the draw rod 152 is pulled upwardly to apply a mechanical load to taper lock the proximal body component 12 and the distal stem component 14 to one another, the force to apply such a load is thus transmitted through the tensile bar component 180 clamped between the collars 232, 234 of the draw bar components 152, 154. Once the force exceeds a predetermined amount, the tensile bar component 180 breaks thereby breaking the mechanical linkage between the draw bar components 152, 154 so as to prevent further load being applied to the proximal body component 12 and the distal stem component 14.

In operation, a surgeon may use the taper assembly instrument 150 in combination with the clamp instrument 60 (or the clamp instrument 100) to apply a mechanical load on the proximal body component 12 and the distal stem component 14 to taper lock them to one another. The surgeon (or other personnel) first assembles the taper assembly instrument 150, including loading a tensile bar component 180 in the instrument 150. To facilitate the step-by-step assembly of the instrument, the taper assembly instrument 150 has a number of alignment indicators disposed on its various components. In the exemplary embodiment described herein, the alignment indicators are shown as a series of arrows, some of which are numbered. Such indicators may be painted on or etched into the outer surface of the various components.

To begin assembling the instrument 150, the surgeon first aligns the distal end 166 of the proximal draw rod component 154 with the proximal end 176 of the distal draw rod component 156 such that the tensile bar slots 164, 174 of the two rod components 154, 156 open into one another. To facilitate such alignment, the surgeon may align an arrow labeled "1" (as in "step 1") disposed on the proximal draw rod component 154 with an arrow disposed on the distal draw rod component 156, as shown in FIGS. 17-20. Once the arrows are aligned with one another, the surgeon pushes the two ends 166, 176 together.

Figure 20:
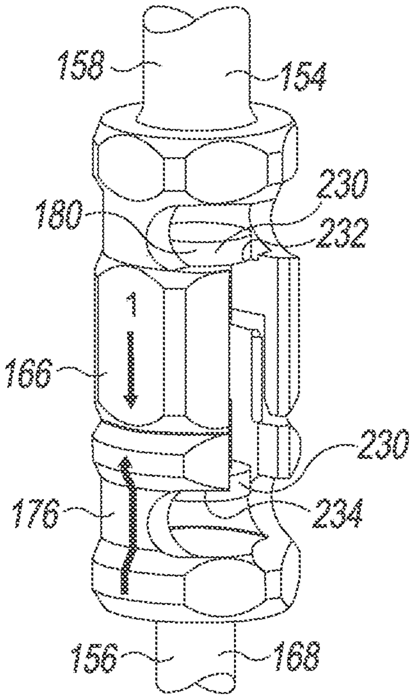
Figure 21:
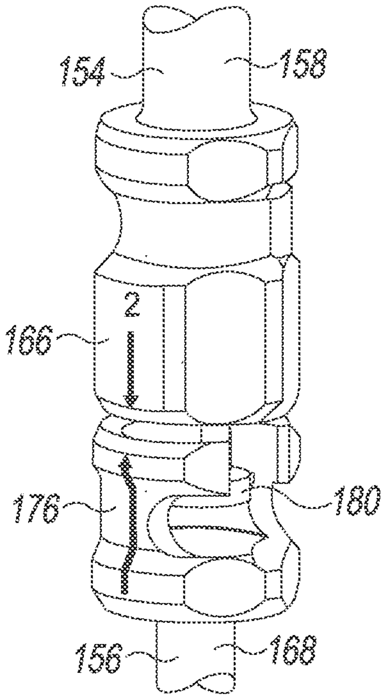
FIG. 21 is view similar to FIGS. 19 and 20, but showing the proximal draw rod component rotated relative to the distal draw rod component so as to capture the tensile bar component in the draw rod.

As shown in FIGS. 19-21, the surgeon then installs the tensile bar component 180 into the cavity 178 created by the tensile bar slots 164, 174. Specifically, the tensile bar component 180 is loaded into the cavity such that the lower surface of the annular flange 230 on the upper end of the tensile bar component 180 abuts the upper surface of the proximal draw rod component's collar 232 and the upper surface of the annular flange 230 on the lower end of the tensile bar component 180 abuts the lower surface of the distal draw rod component's collar 234. Once so positioned, the surgeon rotates the proximal draw rod component 154 relative to the distal draw rod component 156 so as to lock the tensile bar component 180 in the draw rod 152. To facilitate doing so, the surgeon may rotate the proximal draw rod component 154 until an arrow labeled "2" (as in "step 2") disposed on the proximal draw rod component 154 aligns with the arrow disposed on the distal draw rod component 156, as shown in FIG. 21.

Figure 26:
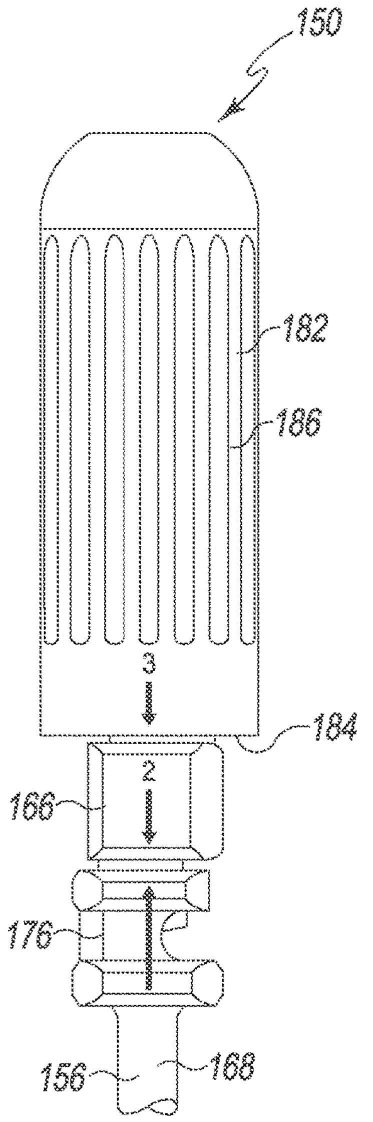
Figure 27:
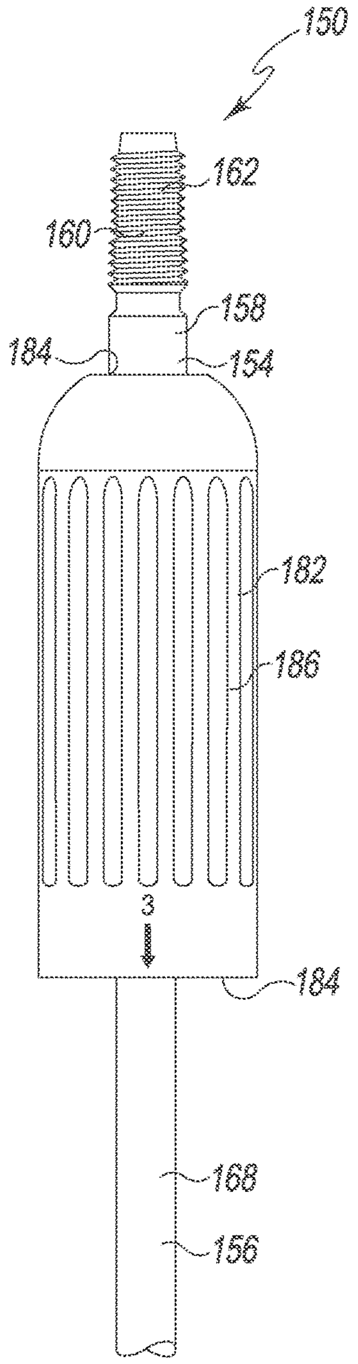

The surgeon may then install the handle 182 on the elongated shaft 158 of the proximal draw rod component 154 by inserting the proximal end 162 of the shaft 158 into the distal end of the handle's bore 184 (as shown in FIGS. 25-27) and thereafter advancing the shaft 158 within the bore 184 until its threaded proximal end 162 exits the proximal end of the bore 184. To facilitate doing so, the surgeon may align an arrow labeled "3" (as in "step 3") disposed on the handle 182 with the arrow labeled "2" disposed on the proximal draw rod component 154 and the arrow disposed on the distal draw rod component 156, as shown in FIG. 26.

Figure 29:
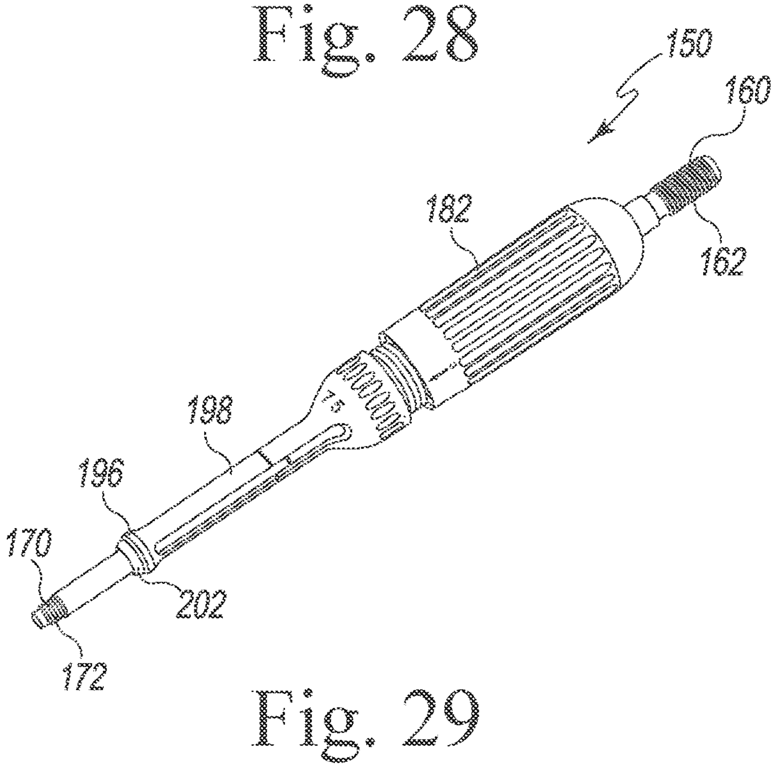
Figure 30:
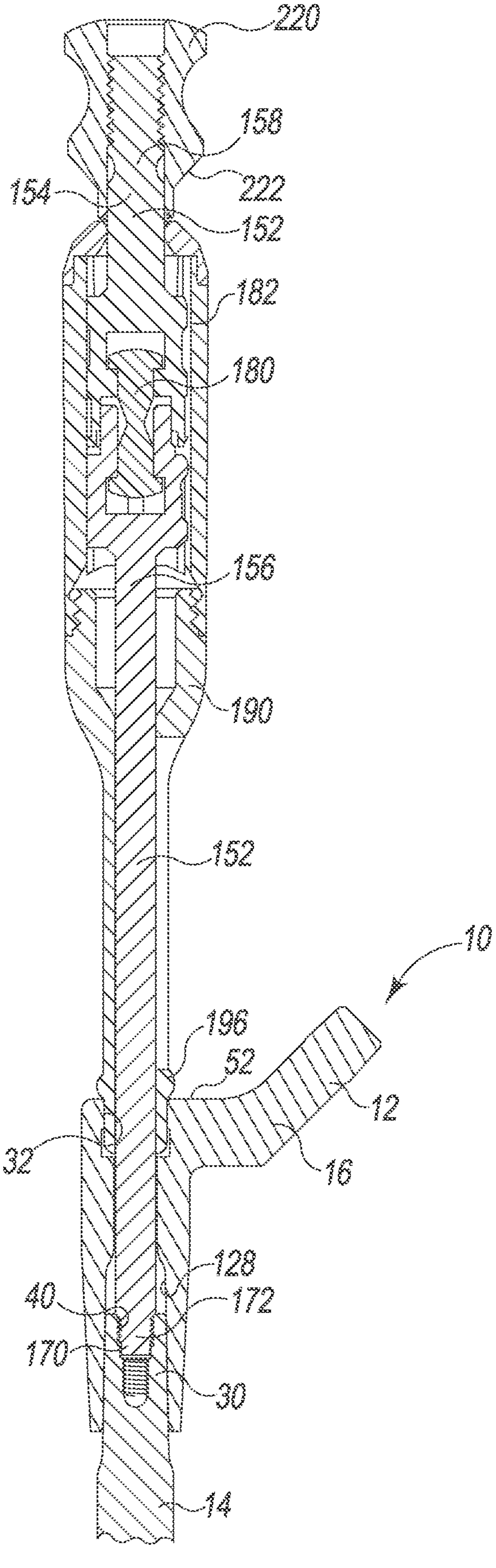
FIG. 30 is a cross sectional view showing the taper assembly instrument of FIG. 15 asserting a load on the proximal body component of FIG. 1 and the distal stem component of FIG. 3 so as to taper lock them to one another.
Figure 31:
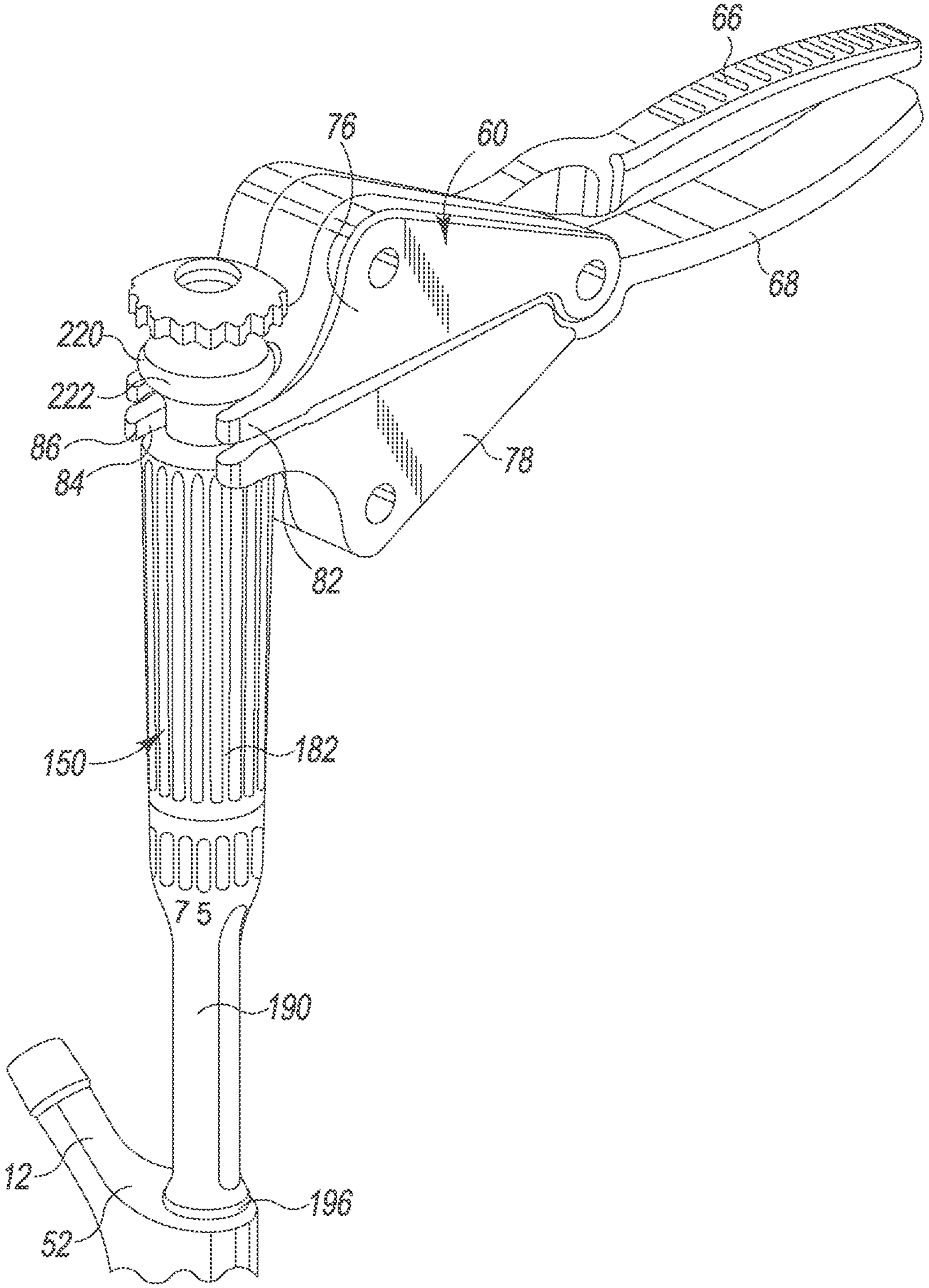
FIG. 31 is a perspective view showing the clamp instrument of FIG. 7 and the taper assembly instrument of FIG. 15 asserting a load on the proximal body component of FIG. 1 and the distal stem component of FIG. 3 so as to taper lock them to one another.

The tip component 190 may then be installed on the elongated shaft 168 of the distal draw rod component 156 by inserting the distal end 172 of the shaft 168 into the proximal end of the tip component's bore 194 (as shown in FIGS. 28 and 29) and thereafter advancing the shaft 168 within the bore 194 until its threaded distal end 172 exits the distal end of the bore 194. The surgeon advances the tip component 190 until the threads 204 formed in its proximal end engage the threads 206 formed in the distal end of the handle 182. Thereafter, the tip component 190 is rotated such that the threads 204, 206 threadingly engage one another thereby screwing the tip component 190 to the handle 182. In doing so, the draw rod 152 is captured in the assembly of the handle 182 and tip component 190. Thereafter, the knob 220 is secured to the threads 160 on the proximal end 162 of the draw rod's proximal draw rod component 154 thereby completing assembly of the taper assembly instrument 150.

The taper assembly instrument 150 is then secured to the proximal body component 12 and the distal stem component 14. To do so, the distal end 202 of the instrument's tip component 190, including the threaded distal end 172 of the distal draw rod component 156 extending out of the tip component 190, is inserted into the countersunk cavity 32 formed in the superior surface 52 of the body 24 of the proximal body component 12. The threads 170 formed in the distal end 172 of the distal draw rod component 156 engage the upper threads 40 formed in the distal stem component 14. The surgeon then rotates the knob 220 to thread the threads 170 of the instrument's draw rod 152 into the threads 40 formed in the distal stem component 14. Doing so draws the draw rod 152 and hence the taper assembly instrument 150 toward the distal stem component 16. As the taper assembly instrument 150 is urged toward the distal stem component 16, the annularly-shaped shoulder 196 that extends outwardly from the outer surface 198 of the tip component 190 engages the superior surface 52 of the body 24 of the proximal body component 12. Because the shoulder 196 has a diameter that is larger than the diameter of the countersunk cavity 32 formed in the superior surface 52 of the body 24 of the proximal body component 12 (see FIG. 30), the shoulder 196 functions as a stop and thus prevents the tip component 190 from being fully received into the countersunk cavity 32.

The surgeon then installs the clamp instrument 60 to the taper assembly instrument 150. To do so, the surgeon positions the clamp instrument such that the section of the draw rod 152 of the taper assembly instrument extending out of the proximal end of the handle and 182 and located in the distal end of the knob 220 is received into the U-shaped opening 86 of the sockets 82, 84 of the clamp instrument's clamping jaws 76, 78. Specifically, the sockets 82, 84 of the clamp instrument 60 are positioned on the draw rod 152 such that the sockets 82, 84 are captured between the knob's annularly-shaped shoulder 222 and the proximal end of the handle 182.

The surgeon then squeezes the handles 66, 68 (i.e., moves them towards one another). By doing so, the clamping jaws 76, 78 pivot relative to one another thereby causing the sockets 82, 84 to be urged or otherwise moved away from one another. Because the sockets 82, 84 are captured between the knob 220 and the handle 182, the knob 220 is urged proximally away from the handle 182 (i.e., upwardly as viewed in the orientation of FIG. 24) as the jaws 76, 78 spread away from one another. Such upward movement of the knob 220 likewise draws the draw rod 152—and hence the distal stem component 14 threaded to it—upwardly thereby urging the stem component's tapered post 30 and the sidewall defining the tapered bore 28 of the proximal body component 12 toward one another. As the distal stem component 14 is urged upwardly against the proximal body component 12 by the upward movement of the draw shaft 152, the superior surface 52 of the body 24 of the proximal body component 12 engages the shoulder 196 formed in the tip component 190 of the taper assembly instrument 150 thereby clamping the proximal body component 12 between the tip component 190 and distal stem component 14.

As the draw rod 152 continues to be drawn upwardly by further squeezing of the handles 66, 68, the force to apply the mechanical load necessary to taper lock the proximal body component 12 and the distal stem component 14 to one another is transmitted through the draw rod 152 and thus the tensile bar component 180 clamped between the collars 232, 234 of the draw bar components 152, 154. Once the force exceeds a predetermined amount, the tensile bar component 180 breaks thereby breaking the mechanical linkage between the draw bar components 152, 154 so as to prevent further load being applied to the proximal body component 12 and the distal stem component 14. Thus, the desired, predetermined load is applied to the two components 12, 14, but additional load is prevented from being applied to them.

Once the components 12, 14 have been taper locked to one another, the surgeon may then install a locking bolt (not shown) to act as a secondary lock between the proximal body component 12 to the distal stem component 14. To do so, the surgeon inserts the locking bolt through the countersunk cavity 32 of the proximal body component 12 and uses finger pressure to turn the locking bolt thereby causing initial thread engagement between the threads of the locking bolt and the lower threads 42 of the distal stem component 14. The surgeon then applies a predetermined torque to the locking bolt to fully seat the same.

It should be appreciated that although taper locking of the components 12, 14 has herein been described by use of the clamp instrument 60, the clamp instrument 100 could also be used in conjunction with the taper assembly instrument 150 in a similar manner to as described above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical clamp instrument operable to taper lock orthopaedic components to one another, comprising:

a first lever having (i) a proximal end that includes an upper handle, and (ii) a distal end that includes a pivot flange link, a second lever pivotally coupled to the first lever, the second lever having a (i) a proximal end that includes a lower handle, and a distal end that includes a pivot flange link, an upper end of the pivot flange link of the second lever being pivotally coupled to a lower end of the pivot flange link of the first lever, a first clamping jaw having (i) a socket formed in a distal end thereof, the socket being configured to receive an orthopaedic taper assembly instrument therein, (ii) an upper end pivotally coupled to an upper end of the pivot flange link of the first lever, and (iii) a proximal end opposite its distal end, and a second clamping jaw having (i) a socket formed in a distal end thereof, the socket being configured to receive the orthopaedic taper assembly instrument therein, (ii) a lower end pivotally coupled to a lower end of the pivot flange link of the second lever, and (iii) a proximal end opposite its distal end and pivotally coupled to the proximal end of the first clamping jaw, wherein movement of the upper handle and the lower handle toward one another causes movement of the socket of the first clamping jaw and the socket of the second clamping jaw away from one another.

2. The orthopaedic surgical clamp instrument of claim 1, wherein:

the upper end of the pivot flange link of the second lever is pivotally coupled to the lower end of the pivot flange of the first lever at a first pivot joint, the proximal end of the second clamping jaw is pivotally coupled to the proximal end of the first clamping jaw at a second pivot joint, and movement of the upper handle and the lower handle toward one another causes movement of the first pivot joint distally away from the second pivot joint.

3. The orthopaedic surgical clamp instrument of claim 2, wherein:

the upper end of the first clamping jaw is pivotally coupled to the upper end of the pivot flange link of the first lever at a third pivot joint, the lower end of the second clamping jaw is pivotally coupled to the lower end of the pivot flange link of the second lever at a fourth pivot joint, and movement of the first pivot joint distally away from the second pivot joint causes movement of the third pivot joint away from the fourth pivot joint.

4. The orthopaedic surgical clamp instrument of claim 1, wherein:

the upper end of the first clamping jaw is pivotally coupled to the upper end of the pivot flange link of the first lever at a first pivot joint, the lower end of the second clamping jaw is pivotally coupled to the lower end of the pivot flange link of the second lever at a second pivot joint, and movement of the upper handle and the lower handle toward one another causes movement of the first pivot joint away from the second pivot joint.

5. The orthopaedic surgical clamp instrument of claim 1, wherein the pivot flange link of the first lever, the pivot flange link of the second lever, the first clamping jaw, and the second clamping jaw define a four-bar linkage.

6. An orthopaedic surgical instrument assembly operable to taper lock orthopaedic components to one another, comprising:

a taper assembly instrument comprising a handle with a draw rod extending therethrough so as to be slidable relative to the handle, the draw bar rod having a knob on its proximal end and a set of locking threads on its distal end, and a clamp instrument configured to selectively engage the taper assembly instrument so as to move the draw rod relative to the handle, the clamp instrument comprising:

a first lever having (i) a proximal end that includes an upper handle, and (ii) a distal end that includes a pivot flange link, a second lever pivotally coupled to the first lever, the second lever having a (i) a proximal end that includes a lower handle, and (ii) a distal end that includes a pivot flange link, an upper end of the pivot flange link of the second lever being pivotally coupled to a lower end of the pivot flange of the first lever, a first clamping jaw having (i) a socket formed in a distal end thereof, the socket being configured to receive the draw rod of the taper assembly instrument therein, (ii) an upper end pivotally coupled to an upper end of the pivot flange link of the first lever, and (iii) a proximal end opposite its distal end, and a second clamping jaw having (i) a socket formed in a distal end thereof, the socket being configured to receive the draw rod of the taper assembly instrument therein, (ii) a lower end pivotally coupled to a lower end of the pivot flange link of the second lever, and (iii) a proximal end opposite its distal end and pivotally coupled to the proximal end of the first clamping jaw.

7. The orthopaedic surgical instrument assembly of claim 6, wherein movement of the upper handle and the lower handle of the clamp instrument toward one another causes movement of the socket of the first clamping jaw and the socket of the second clamping jaw away from one another such that, when the draw rod of the of the taper assembly instrument is positioned in the socket of the first clamping jaw and the socket of the second clamping jaw, the knob of the taper assembly instrument is urged away from the handle of the of the taper assembly instrument.

8. The orthopaedic surgical instrument assembly of claim 6, wherein:

the upper end of the pivot flange link of the second lever is pivotally coupled to the lower end of the pivot flange of the first lever at a first pivot joint, the proximal end of the second clamping jaw is pivotally coupled to the proximal end of the first clamping jaw at a second pivot joint, and movement of the upper handle and the lower handle toward one another causes movement of the first pivot joint distally away from the second pivot joint.

9. The orthopaedic surgical instrument assembly of claim 8, wherein:

the upper end of the first clamping jaw is pivotally coupled to the upper end of the pivot flange link of the first lever at a third pivot joint, the lower end of the second clamping jaw is pivotally coupled to the lower end of the pivot flange link of the second lever at a fourth pivot joint, and movement of the first pivot joint distally away from the second pivot joint causes movement of the third pivot joint away from the fourth pivot joint.

10. The orthopaedic surgical instrument assembly of claim 6, wherein:

the upper end of the first clamping jaw is pivotally coupled to the upper end of the pivot flange link of the first lever at a first pivot joint, the lower end of the second clamping jaw is pivotally coupled to the lower end of the pivot flange link of the second lever at a second pivot joint, and movement of the upper handle and the lower handle toward one another causes movement of the first pivot joint away from the second pivot joint.

11. The orthopaedic surgical instrument assembly of claim 6, wherein the pivot flange link of the first lever, the pivot flange link of the second lever, the first clamping jaw, and the second clamping jaw define a four-bar linkage.

12. An orthopaedic surgical clamp instrument operable to taper lock orthopaedic components to one another, comprising:

a first clamping jaw having (i) a socket formed in a distal end thereof, the socket being configured to receive an orthopaedic taper assembly instrument therein, and (ii) a proximal end opposite its distal end, a second clamping jaw having (i) a socket formed in a distal end thereof, the socket being configured to receive the orthopaedic taper assembly instrument therein, and (ii) a proximal end opposite its distal end and pivotally coupled to the proximal end of the first clamping jaw, a drive link operatively coupled to the first clamping jaw and the second connecting jaw, the drive link having a threaded bore formed therein, and a first connecting link and a second connecting link, wherein: (i) an upper end of the first connecting link is pivotally coupled to the first clamping jaw at a first pivot joint, (ii) a lower end of the first connecting link is pivotally coupled to the drive link, (iii) a lower end of the second connecting link is pivotally coupled to the second clamping jaw at a second pivot joint, and (iv) an upper end of the second connecting link is pivotally coupled to the drive link, a drive screw having (i) a connector configured to be secured to a rotary tool defined in its proximal end and (ii) a threaded shaft extending distally away from the connector, the threaded shaft of the drive screw being positioned in the threaded bore of the drive link, wherein (i) rotation of the drive screw in a first direction causes the first and second pivot joints to be moved away from one another thereby moving the first and second clamping jaws away from one another, and (ii) rotation of the drive screw in a second, opposite direction causes the first and second pivot joints to be moved toward one another thereby moving the first and second clamping jaws toward one another.

13. The orthopaedic surgical clamp instrument of claim 12, wherein:

the lower end of the first connecting link and the upper end of the second connecting link are pivotally coupled to the drive link at a third pivot joint, the proximal end of the second clamping jaw is pivotally coupled to the proximal end of the first clamping jaw at a fourth pivot joint, rotation of the drive screw in the first direction causes the third and fourth pivot joints to be moved toward one another thereby moving the first and second clamping jaws away from one another, and rotation of the drive screw in the second, opposite direction causes the third and fourth pivot joints to be moved away from one another thereby moving the first and second clamping jaws toward one another.

* * * * *